(12) United States Patent
Ahn

(10) Patent No.: US 8,236,983 B2
(45) Date of Patent: Aug. 7, 2012

(54) COMPOSITION AND METHOD FOR THE TREATMENT OF DISEASES AFFECTED BY APOPTOSIS

(75) Inventor: Jung-Mo Ahn, Richardson, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 477 days.

(21) Appl. No.: 12/353,173

(22) Filed: Jan. 13, 2009

(65) Prior Publication Data
US 2010/0178324 A1 Jul. 15, 2010

Related U.S. Application Data

(63) Continuation-in-part of application No. 12/048,197, filed on Mar. 13, 2008.

(51) Int. Cl.
*C07C 229/60* (2006.01)
*C07C 271/28* (2006.01)

(52) U.S. Cl. .............. 562/453; 560/24; 560/27; 560/45; 560/46

(58) Field of Classification Search .................. None
See application file for complete search history.

(56) References Cited

FOREIGN PATENT DOCUMENTS

| WO | 2008-112938 A2 | 9/2008 |
| WO | 2008-112939 A1 | 9/2008 |
| WO | 2008-112941 A1 | 9/2008 |

OTHER PUBLICATIONS

Plante et al., Org. & Biomol. Chem., (2008), 6, p. 138-146.*
Database CAPLUS on STN, Acc. No. 2007:1424768, Plante et al., Organic & Biomolecular Chemistry (2008), 6(1), p. 138-146 (abstract).*
Adams, J. M. , et al., "Life-or-death decisions by the Bcl-2 protein family." Trends Biochem. Sci. (2001), 26:61-66.
Chittenden, T. , et al., "A conserved domain in Bak, distinct from BH1 and BH2, mediates cell death and protein binding Functions," EMBO J. (1995), 14:5589-5596.
Cochran, A., "Antagonists of protein-protein interactions." Chem. Biol. (2000), 7:R85-R94.
Kussie, P. H., et al., "Structure of the MDM2 Oncoprotein Bound to the p53 Tumor Suppressor Transactivation Domain," Science (1996), 274:948-953.
Kutzki, O. , et al., "Development of a Potent Bcl-xL Antagonist Based on α-Helix Mimicry" J. Am. Chem. Soc. (2002), 124:11838-11839.
Sattler, M. , et al., "Structure of Bcl-xL-Bak Peptide Complex: Recognition Between Regulators of Apoptosis." Science (1997), 275:983-986.
Walensky, L. D., et al., "Activation of Apoptosis in Vivo by a Hydrocarbon-Stapled BH3 Helix," Science (2004), 305:1466-1470.
Yin, H. , et al., "Terphenyl-Based Helical Mimetics That Disrupt the p53/HDM2 Interaction," Angew. Chem. Int. Ed., 44 (2005) 2704-2707.
Yin, H., et al., "Terephthalamide Derivatives as Mimetics of Helical Peptides: Disruption of the Bcl-xL/Bak Interaction." J. Am. Chem. Soc (2005), 127:5463-5468.
Yin, H., et al., "Terphenyl-based Bak BH3 α-helical proteomimetics as low-molecular-weight antagonists of Bcl-xL." J. Am. Chem. Soc (2005), 127:10191-10196.
International Search Report and Written Opinion for PCT/US2009/020898 dateds Aug. 20, 2010.
Ahn, J-M, et al., "Facile synthesis of benzamides to mimic an α-helix," Tetrahedron Letters (2007)m 48:3543-3547.
Saraogi, I., et al., "Synthetic α-Helix Mimetics as Agonists and Antagonists of Islet Amyloid Polypeptide Aggregation," Angewandte Chemie (2010)m 49:736-739.

* cited by examiner

*Primary Examiner* — Brian J Davis
(74) *Attorney, Agent, or Firm* — Fulbright & Jaworski

(57) ABSTRACT

The present invention includes methods of making and methods of using peptidomimetics compositions that mimic α-helical BH3 sequences in cells. The peptidomimetics can be used to mimic α-helical BH3 sequences and kill cancer cells.

6 Claims, 14 Drawing Sheets

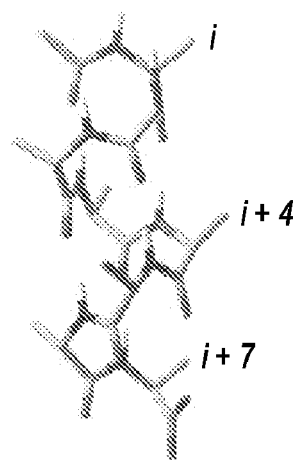 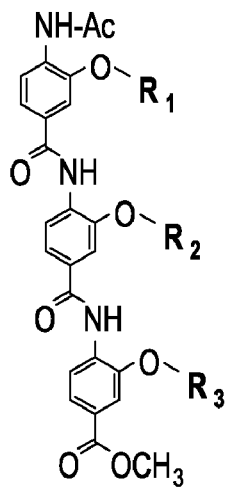  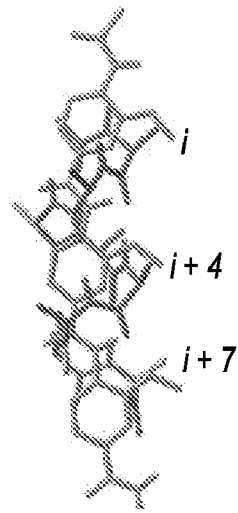
FIG. 1A   FIG. 1B   FIG. 1C   FIG. 1D
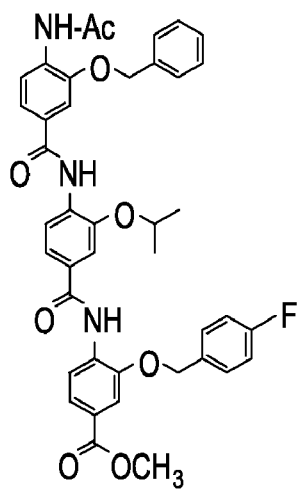 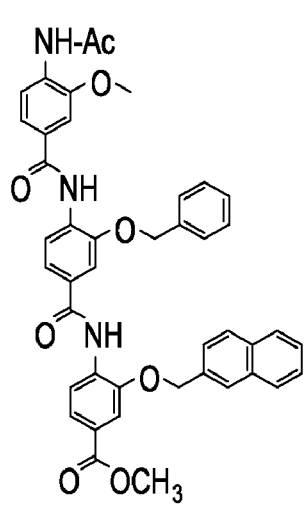 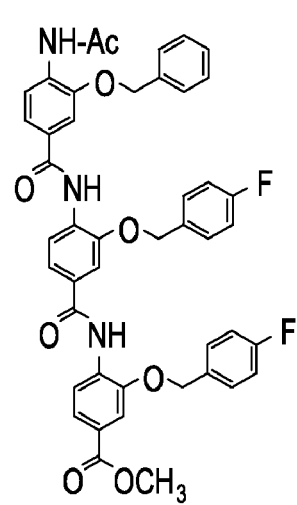
FIG. 1E 1   FIG. 1E 2   FIG. 1E 3

COMPOSITION AND METHOD FOR THE TREATMENT OF DISEASES AFFECTED BY APOPTOSIS

CROSS-REFERENCE TO RELATED APPLICATIONS

This application is a continuation-in-part of application Ser. No. 12/048,197, filed on Mar. 13, 2008, now pending.

TECHNICAL FIELD OF THE INVENTION

The present invention relates in general to the field of peptidomimetics, specifically to compositions of matter and methods of making and using analogues for the treatment of diseases affected by apoptosis or cell proliferation.

STATEMENT OF FEDERALLY FUNDED RESEARCH

None.

INCORPORATION-BY-REFERENCE OF MATERIALS FILED ON COMPACT DISC

None.

BACKGROUND OF THE INVENTION

Without limiting the scope of the invention, its background is described in connection with apoptosis. Apoptosis-(also called programmed cell death) plays a role in many diseases including developmental, tissue homeostasis, and degenerative diseases. Apoptosis is generally a directed process where the cell actively destroys itself in response to extracellular signals. Generally, apoptosis is characterized by the ordered cellular degradation of proteins and organelles, maintenance of plasma membrane integrity, and non-inflammatory phagocytosis of the cell.

Some types of cancer cells have been characterized by defects in the normal control of apoptosis. One example is the anti-apoptotic gene bcl-2. Enhanced expression of Bcl-2 provides resistance to apoptosis by suppressing the activation of the proapoptotic Bcl-2 related proteins Bax and Bak, which are essential in apoptosis initiated from both mitochondria and the endoplasmic reticulum. BH3 proteins are a member of the Bcl-2 family of protein with multidomain proapoptotic members Bax and Bak that release cytochrome c from mitochondria and kill cells. The BH3 domains capable of inducing oligomerization of to release cytochrome c. Bak as well as Bax, Bad, Bid and etc. are members of the pro-apoptotic proteins and known to have the BH3 domain to interact with anti-apoptotic Bcl proteins. (Adams, J. M.; Cory, S., Life-or-death decisions by the Bcl-2 protein family. Trends Biochem. Sci. 2001, 26, 61-66). These protein complexes like Bcl/Bak are a key element to regulate programmed cell death. Overexpression of the anti-apoptotic proteins Bcl-2 and Bcl-xL is commonly observed in human cancers.

SUMMARY OF THE INVENTION

The present invention provides peptidomimetics compositions that mimic α-helical BH3 sequences in cells. The peptidomimetics can be used to mimic α-helical BH3 sequences and kill cancer cells.

The present invention provides an oligo-benzamide compound comprising the formula:

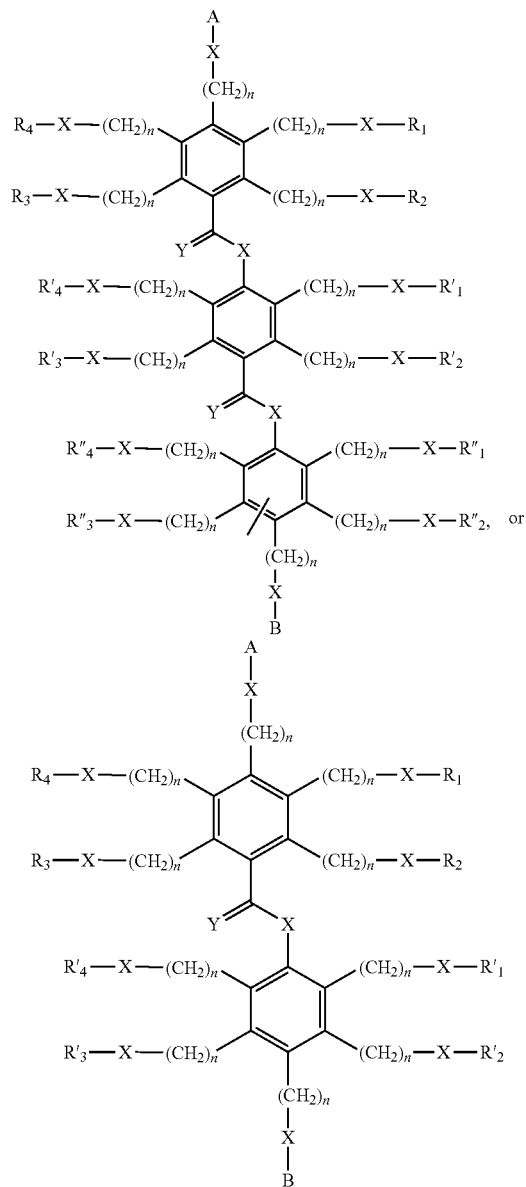

wherein R1, R2, R3, R4, R'1, R'2, R'3, R'4, R"1, R"2, R"3, and R"4 independently comprise a H, one or more optionally substituted alkyl groups, lower alkyl groups, alkoxy groups, alkoxyalkyl groups, hydroxy groups, hydroxyalkyl groups, alkenyl groups, amino groups, imino groups, urea groups, nitrate groups, alkylamino groups, nitroso groups, aryl groups, biaryl groups, bridged aryl groups, fused aryl groups, alkylaryl groups, arylalkyl groups, arylalkoxy groups, arylalkylamino groups, cycloalkyl groups, bridged cycloalkyl groups, cycloalkoxy groups, cycloalkyl-alkyl groups, arylthio groups, alkylthio groups, alkylsulfinyl groups, alkylsulfonyl groups, arylsulfonyl groups, arylsulfinyl groups, caboxamido groups, carbamoyl groups, carboxyl groups, carbonyl groups, alkoxycarbonyl groups, halogen groups, haloalkyl groups, haloalkoxy groups, heteroayl, heterocyclic ring, arylheterocyclic ring, heterocyclic compounds, amido, imido, guanidino, hydrazido, aminoxy, alkoxyamino, alkylamido, carboxylic ester groups, thioethers groups, carboxylic acids, phosphoryl groups, polycyclic aromatic substituted with a OH, $NH_2$, SH, F, Cl, Br, I, NHR, NRR', $CN_3H_4$, a N, a O, a S, a H, or combination thereof; "X" independently comprise a C, a N, a O, a S, a H, —CH$_2$—, —CH$_2$CH$_2$—, —CH=CH—, —C≡C—, —NH—, —NR—, —NH—NH—, —NH(CH$_2$)$_n$NH, —NR(CH$_2$)$_n$NR'— —NR—NR'—, —NH—O—, —NR—O—, —NH(CH$_2$)$_n$O—, —NR(CH$_2$)$_n$O—, —NH(CH$_2$)$_n$S—, —NR(CH$_2$)$_n$S—, —O(CH$_2$)$_n$O—, —O(CH$_2$)$_n$S—, —S(CH$_2$)$_n$S—, —CO—, —CO$_2$—, —COS—, —CONH—, —CONR—, —OC(O)NH—, —NHCONH—, —CONHCO—, —CO(CH$_2$)$_n$CO—, or combination thereof; "Y" independently comprise a N, a O, a C, a S or 2Hs; "n" is 0, 1, 2, 3, 4, 5, 6, 7 or more; and "A" and "B" independently comprises R1, R2, R3, R4, R'1, R'2, R'3, R'4, R"1, R"2, R"3, and R"4, an acetyl, a Boc (t-butoxycarbonyl), a Fmoc (9-fluorenylmethoxycarbonyl), a Cbz (benzyloxycarbonyl), an Aloc (allyloxycarbonyl), an amino acid, an amino acid analogue, an artificial amino acid, a peptide of 2-30 amino acids, a carbohydrate, a lipid, a nucleic acid, a sugar, a linker of 1-30 amino acids, a linker of an optionally substituted lower alkyl, a linker of an optionally substituted C1-C7 alkyl, a linker as seen below

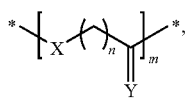

wherein "Y" comprises a N, a O, a C, a S or 2Hs.

A method of treating a diseases affected by apoptosis by identifying a subject in need of treatment for a diseases affected by apoptosis and supplying an affective amount of an oligo-benzamide compound, wherein the oligo-benzamide compound comprises the formula:

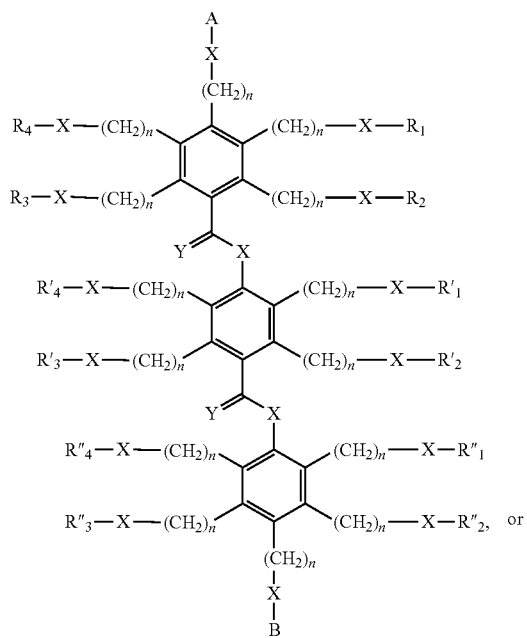

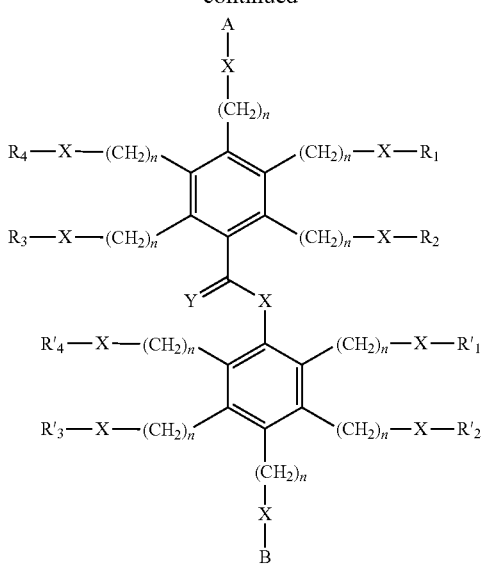

wherein R1, R2, R3, R4, R'1, R'2, R'3, R'4, R"1, R"2, R"3, and R"4 independently comprise H, one or more optionally substituted alkyl groups, lower alkyl groups, alkoxy groups, alkoxyalkyl groups, hydroxy groups, hydroxyalkyl groups, alkenyl groups, amino groups, imino groups, urea groups, nitrate groups, alkylamino groups, nitroso groups, aryl groups, biaryl groups, bridged aryl groups, fused aryl groups, alkylaryl groups, arylalkyl groups, arylalkoxy groups, arylalkylamino groups, cycloalkyl groups, bridged cycloalkyl groups, cycloalkoxy groups, cycloalkyl-alkyl groups, arylthio groups, alkylthio groups, alkylsulfinyl groups, alkylsulfonyl groups, arylsulfonyl groups, arylsulfinyl groups, caboxamido groups, carbamoyl groups, carboxyl groups, carbonyl groups, alkoxycarbonyl groups, halogen groups, haloalkyl groups, haloalkoxy groups, heteroayl, heterocyclic ring, arylheterocyclic ring, heterocyclic compounds, amido, imido, guanidino, hydrazido, aminoxy, alkoxyamino, alkylamido, carboxylic ester groups, thioethers groups, carboxylic acids, phosphoryl groups, polycyclic aromatic substituted with a OH, NH$_2$, SH, F, Cl, Br, I, NHR, NRR', CN$_3$H$_4$, a N, a O, a S, a H, or combination thereof, "X" independently comprise a C, a N, a O, a S, a H, —CH$_2$—, —CH$_2$CH$_2$—, —CH=CH—, —C≡C—, —NH—, —NR—, —NH—NH—, —NH(CH$_2$)$_n$NH, —NR(CH$_2$)$_n$NR'— —NR—NR'—, —NH—O—, —NR—O—, —NH(CH$_2$)$_n$O—, —NR(CH$_2$)$_n$O—, —NH(CH$_2$)$_n$S—, —NR(CH$_2$)$_n$S—, —O(CH$_2$)$_n$O—, —O(CH$_2$)$_n$S—, —S(CH$_2$)$_n$S—, —CO—, —CO$_2$—, —COS—, —CONH—, —CONR—, —OC(O)NH—, —NHCONH—, —CONHCO—, —CO(CH$_2$)$_n$CO—, or combination thereof; "Y" independently comprise a N, a O, a C, a S or 2Hs; "n" is 0, 1, 2, 3, 4, 5, 6, 7 or more; and "A" and "B" independently comprises R1, R2, R3, R4, R'1, R'2, R'3, R'4, R"1, R"2, R"3, and R"4, an acetyl, a Boc (t-butoxycarbonyl), a Fmoc (9-fluorenylmethoxycarbonyl), a Cbz (benzyloxycarbonyl), an Aloc (allyloxycarbonyl), an amino acid, an amino acid analogue, an artificial amino acid, a peptide of 2-30 amino acids, a carbohydrate, a lipid, a nucleic acid, a sugar, a linker of 1-30 amino acids, a linker of an optionally substituted lower alkyl, a linker of an optionally substituted C1-C7 alkyl, a linker as seen below and wherein "Y" comprises a N, a O, a C, a S or 2Hs.

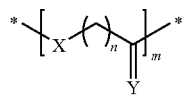

A method of making an oligo-benzamide compound is reacting a first optionally substituted 4-amino benzoic acid compound with a second optionally substituted alkyl 4-amino benzoate compound to form a bis-benzamide. Upon hydrolysis of the alkyl ester, the bis-benzamide can further be reacted with a third optionally substituted alkyl 4-amino benzoate compound to form a tris-benzamide compound, wherein the first optionally substituted 4-amino benzoic acid compound, second optionally substituted alkyl 4-amino benzoate compound, and third optionally substituted alkyl 4-amino benzoate compound are individually substituted with a C, a N, a O, a S, a H, optionally substituted alkyl groups, lower alkyl groups, alkoxy groups, alkoxyalkyl groups, hydroxy groups, hydroxyalkyl groups, alkenyl groups, amino groups, imino groups, urea groups, nitrate groups, alkylamino groups, nitroso groups, aryl groups, biaryl groups, bridged aryl groups, fused aryl groups, alkylaryl groups, arylalkyl groups, arylalkoxy groups, arylalkylamino groups, cycloalkyl groups, bridged cycloalkyl groups, cycloalkoxy groups, cycloalkyl-alkyl groups, arylthio groups, alkylthio groups, alkylsulfinyl groups, alkylsulfonyl groups, arylsulfonyl groups, arylsulfinyl groups, caboxamido groups, carbamoyl groups, carboxyl groups, carbonyl groups, alkoxycarbonyl groups, halogen groups, haloalkyl groups, haloalkoxy groups, heteroayl, heterocyclic ring, arylheterocyclic ring, heterocyclic compounds, amido, imido, guanidino, hydrazido, aminoxy, alkoxyamino, alkylamido, carboxylic ester groups, thioethers groups, carboxylic acids, phosphoryl groups, polycyclic aromatic, substituted polycyclic aromatic, an acetyl, Boc (t-butoxycarbonyl), a Fmoc (9-fluorenyl-methoxycarbonyl), a Cbz (benzyloxycarbonyl), an Aloc (allyloxycarbonyl), an amino acid, an amino acid analogue, an artificial amino acid, a dipeptide, a tripeptide, a tetrapeptide, a pentapeptide, a linker of 1-30 amino acids, a linker of an optionally substituted lower alkyl, a linker of an optionally substituted C1-C7 alkyl, a polycyclic aromatic substituted with a OH, a $NH_2$, a SH, a F, a Cl, a Br, a I, a NHR, a NRR', a $CN_3H_4$, a N, a O, a S, a H, a linker of 1-30 amino acids, an optionally substituted C1-C7 alkyl, an optionally substituted linker as seen below

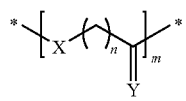

wherein X comprises a N, a O, a C, a S, a H, —$CH_2$—, —$CH_2CH_2$—, —CH=CH—, —C≡C—, —NH—, —NR—, —NH—NH—, —NH$(CH_2)_n$NH, —NR$(CH_2)_n$NR'—, —NR—NR'—, —NH—O—, —NR—O—, —NH$(CH_2)_n$O—, —NR$(CH_2)_n$O—, —NH$(CH_2)_n$S—, —NR$(CH_2)_n$S—, —O$(CH_2)_n$O—, —O$(CH_2)_n$S—, —S$(CH_2)_n$S—, —CO—, —$CO_2$—, —COS—, —CONH—, —CONR—, —OC(O)NH—, —NHCONH—, —CONHCO—, —CO$(CH_2)_n$CO—, or combination thereof; and Y comprises a N, a O, a C, a S, 2Hs or a combination thereof.

BRIEF DESCRIPTION OF THE DRAWINGS

For a more complete understanding of the features and advantages of the present invention, reference is now made to the detailed description of the invention along with the accompanying figures and in which:

FIGS. 1A-1E are images of the structure of oligo-benzamide α-helix peptidomimetic compounds that represent one α-helical face of a peptide or protein;

FIG. 2 is a comparison of the sequence of the BH3 domain from Bad, Bak, Bax, Bcl-2, Bcl-xL, Bid, Bik, and Mcl-1 proteins;

DETAILED DESCRIPTION OF THE INVENTION

Figure 3:
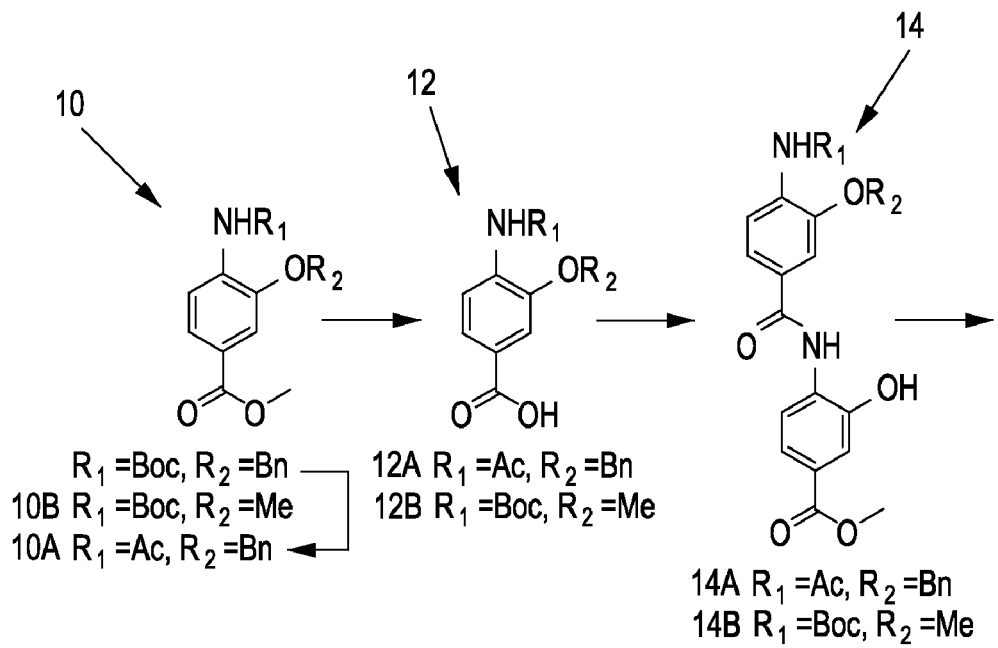
FIG. 3 is a synthesis scheme for the preparation of oligo-benzamide peptidomimetic compounds of the present invention that represent one α-helical face of a peptide or protein.
Figure 3:
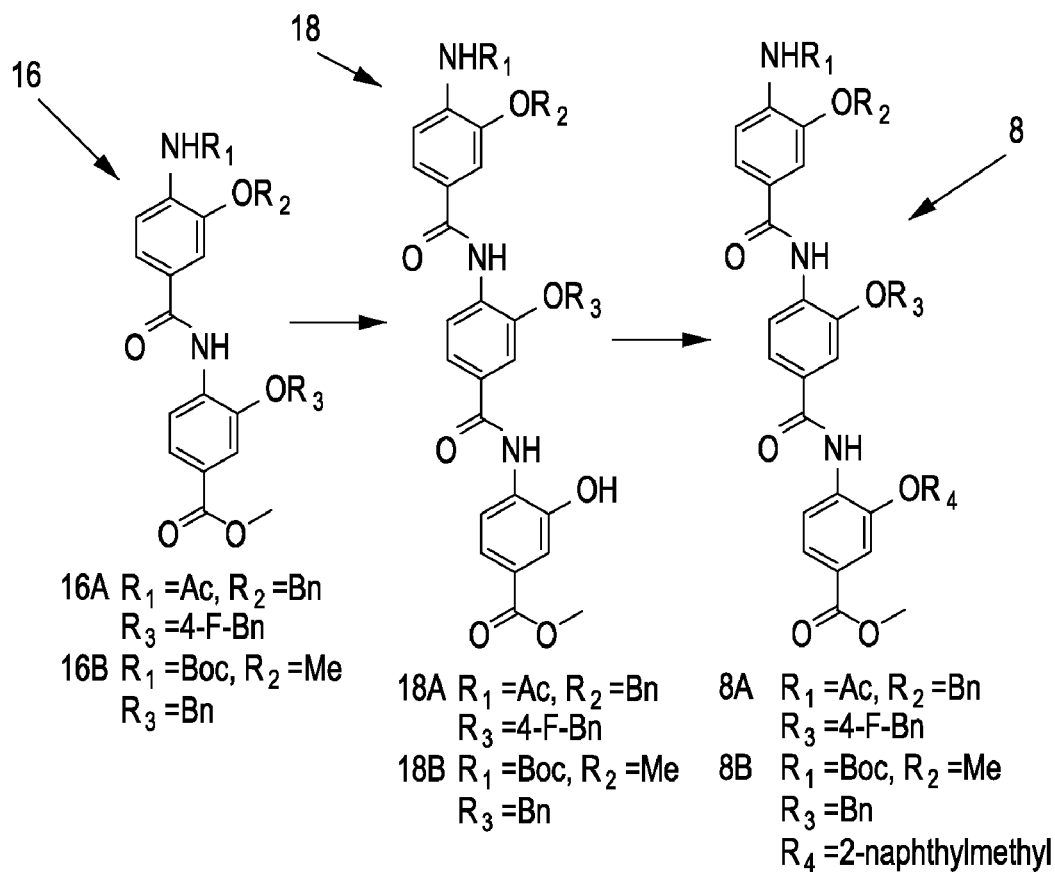

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "Alkyl" denotes branched or unbranched hydrocarbon chains, having between about 1-20 carbons, with "lower Alkyl" denoting branched or unbranched hydrocarbon chains, having between about 1-10 carbons. Non-limiting examples include methyl, ethyl, propyl, n-propyl, isopropyl, butyl, n-butyl, sec-butyl, isobutyl, t-butyl, 1-methylpropyl, pentyl, isopentyl, sec-pentyl, 2-methylpentyl, hexyl, heptyl, octyl, nonyl, decyl, octa-decyl and so on. Alkyl includes cycloalkyl, such as cyclopropyl, cyclobutyl, cyclopentyl, and cyclohexyl. These groups can be optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, carboxamidyl, alkoxycarbonyl, carbamoyl, hydroxamate, alkyl, alkenyl, alkynyl, nitro, amino, alkoxy, amido, imino, imido, guanidino, hydrazido, aminoxy, alkoxyamino, urea, and the like to form alkyl groups such as trifluoro methyl, 3-hydroxyhexyl, 2-carboxypropyl, 2-fluoroethyl, carboxymethyl, cyanobutyl and the like.

As used herein, the term "Aryl" denotes a chain of carbon atoms which form at least one aromatic ring having between about 4-20 carbon atoms, such as phenyl, naphthyl, biphenyl, anthracenyl, pyrenyl, tetrahydronaphthyl, and so on, any of which may be optionally substituted. Aryl also includes arylalkyl groups such as benzyl, phenethyl, and phenylpropyl. Aryl includes a ring system containing an optionally substituted 5 or 6-membered carbocyclic aromatic ring, said system may be bicyclic, polycyclic, bridge, and/or fused. The system may include rings that are aromatic, or partially or completely saturated. Examples of ring systems include phenyl, naphtyl, biphenyl, anthracenyl, pyrenyl, imidazolyl, triazolyl, tetraazolyl, oxazolyl, thiophenyl, pyridyl, pyrrolyl, furanyl, quinolyl, quinolinyl, indenyl, pentalenyl, 1,4-dihydronaphthyl, indanyl, benzimidazolyl, benzothiophenyl, indolyl, benzofuranyl, isoquinolinyl, and so on. The group may be substituted with one or more functional groups which are attached commonly to such chains, such as boronyl, hydroxyl, bromo, fluoro, chloro, iodo, mercapto or thio, cyano, cyanoamido, alkoxy, alkylthio, heterocycle, aryl, heteroaryl, carboxyl, carbalkoyl, carboxamidyl, alkoxycarbonyl, carbamyl, hydroxamate, alkyl, alkenyl, alkynyl, nitro, amino, alkoxy, amido, imino, imido, guanidino, hydrazido, aminoxy, alkoxyamino, urea, and the like to form aryl groups such as biphenyl, iodobiphenyl, methoxybiphenyl, anthryl, bromophenyl, iodophenyl, chlorophenyl, hydroxyphenyl, methoxyphenyl, formylphenyl, acetylphenyl, trifluoromethylthiophenyl, trifluoromethoxyphenyl, alkylthiophenyl, trialkylammoniumphenyl, aminophenyl, amidophenyl, thiazolylphenyl, oxazolylphenyl, imidazolylphenyl, imidazolylmethylphenyl, and the like.

As used herein, the term "Alkenyl" includes optionally substituted straight chain and branched hydrocarbons having between about 1-50 carbons as above with at least one carbon-carbon double bond ($sp^2$). Alkenyls include ethenyl (or vinyl), prop-1-enyl, prop-2-enyl (or allyl), isopropenyl (or 1-methylvinyl), but-1-enyl, but-2-enyl, butadienyls, pentenyls, hexa-2,4-dienyl, and so on. Hydrocarbons having a mixture of double bonds and triple bonds, such as 2-penten-4-ynyl, are grouped as alkynyls herein. Alkenyl includes cycloalkenyl. Cis and trans or (E) and (Z) forms are included within the invention. These groups can be optionally substituted with one or more functional groups which are attached commonly to such chains, such as, boronyl, hydroxyl, bromo, fluoro, chloro, iodo, mercapto or thio, cyano, alkoxy, alkylthio, heterocyclyl, aryl, heteroaryl, carboxyl, carbalkoyl, carboxamidyl, alkoxycarbonyl, carbamoyl, hydroxamate, alkyl, alkenyl, alkynyl, nitro, amino, alkoxy, amido, imino, imido, guanidino, hydrazido, aminoxy, alkoxyamino, urea, and the like to form alkyl groups such as trifluoro methyl, 3-hydroxyhexyl, 2-carboxypropyl, 2-fluoroethyl, carboxymethyl, cyanobutyl and the like.

As used herein, the term "Alkynyl" includes optionally substituted straight chain and branched hydrocarbons having between about 1-50 carbons as above with at least one carbon-carbon triple bond (sp). Alkynyls include ethynyl, propynyls, butynyls, and pentynyls. Hydrocarbons having a mixture of double bonds and triple bonds, such as 2-penten-4-ynyl, are grouped as alkynyls herein. Alkynyl does not include cycloalkynyl. These groups can be optionally substituted with one or more functional groups which are attached commonly to such chains, such as, boronyl, hydroxyl, bromo, fluoro, chloro, iodo, mercapto or thio, cyano, alkoxy, alkylthio, heterocyclyl, aryl, heteroaryl, carboxyl, carbalkoyl, carboxamidyl, alkoxycarbonyl, carbamoyl, hydroxamate, alkyl, alkenyl, alkynyl, nitro, amino, alkoxy, amido, imino, imido, guanidino, hydrazido, aminoxy, alkoxyamino, urea, and the like to form alkyl groups such as trifluoro methyl, 3-hydroxyhexyl, 2-carboxypropyl, 2-fluoroethyl, carboxymethyl, cyanobutyl and the like.

As used herein, the term "Alkoxy" includes an optionally substituted straight chain or branched alkyl group having between about 1-25 carbons with a terminal oxygen linking the alkyl group to the rest of the molecule. Alkoxy includes methoxy, ethoxy, propoxy, isopropoxy, butoxy, t-butoxy, pentoxy and so on. Alkyoxy also includes any substituted alkyl group connected by an ether linkage, such as aminobutoxy, carboxyethoxy, hydroxyethoxy and so on. "Aminoalkyl", "thioalkyl", and "sulfonylalkyl" are analogous to alkoxy, replacing the terminal oxygen atom of alkoxy with, respectively, NH (or NR), S, Se, and $SO_2$. Heteroalkyl includes alkoxy, aminoalkyl, thioalkyl, selenoalkyl, and so on.

As used herein, the terms "cancer" means an increase in the number of abnormal cells derived from a given normal tissue or any clinical definition. In addition, it may involve the invasion of adjacent or non-adjacent tissues and/or the lymphatic or blood-borne spread of malignant cells to other sites and/or regional lymph nodes. Furthermore, the term also encompasses hyperplasia, precancerous cells and minor preneoplastic changes.

As used herein, the term "preventing cancer" means to inhibit the transformation of a cell into an abnormal cell by a carcinogenic agent or agents and/or to inhibit the accumulation of cells expressing cancer-specific genes to a number that creates one or more clinical symptoms associated with cancer.

As used herein, the terms "treating cancer" and "treatment of cancer" mean to at least partially inhibit the replication of cancer cells, to inhibit the spread of cancer, to decrease tumor size, to lessen or reduce the number of cancerous cells in the body, to ameliorate or alleviate the symptoms of the disease caused by the cancer. The treatment is considered therapeutic if there is a decrease in mortality and/or morbidity.

As used herein, the term "pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

As used herein, the term "Pharmaceutically Acceptable Salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartatic acid, citric acid, benzoic acid, o-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically Acceptable Salts also include base addition salts, which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

The present invention provides an oligo-benzamide compound comprising the formula:

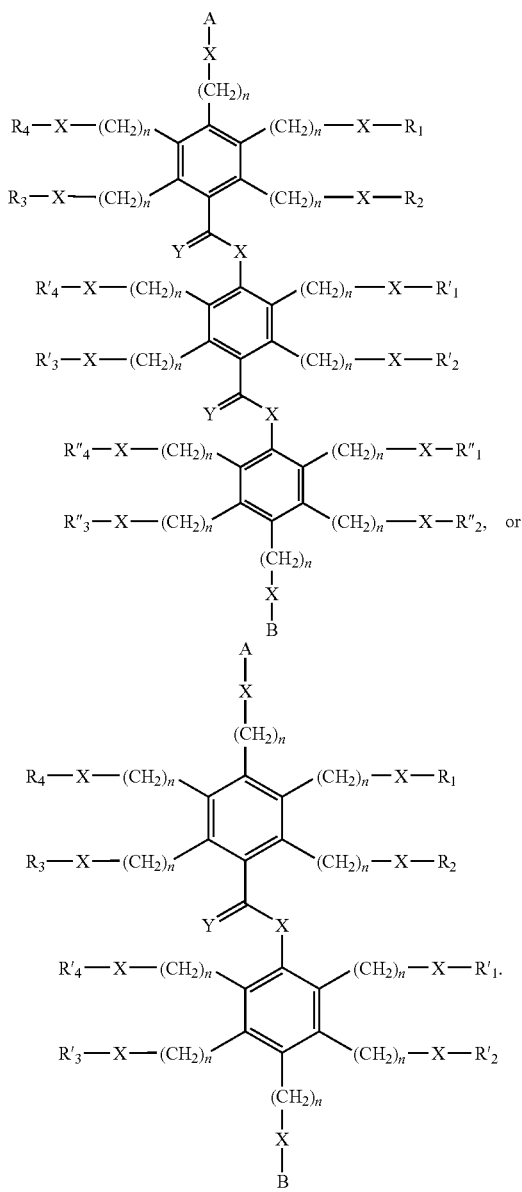

wherein R1, R2, R3, R4, R'1, R'2, R'3, R'4, R"1, R"2, R"3, and R"4 independently comprise a H, one or more optionally substituted alkyl groups, lower alkyl groups, alkoxy groups, alkoxyalkyl groups, hydroxy groups, hydroxyalkyl groups, alkenyl groups, amino groups, imino groups, urea groups, nitrate groups, alkylamino groups, nitroso groups, aryl groups, biaryl groups, bridged aryl groups, fused aryl groups, alkylaryl groups, arylalkyl groups, arylalkoxy groups, arylalkylamino groups, cycloalkyl groups, bridged cycloalkyl groups, cycloalkoxy groups, cycloalkyl-alkyl groups, arylthio groups, alkylthio groups, alkylsulfinyl groups, alkylsulfonyl groups, arylsulfonyl groups, arylsulfinyl groups, caboxamido groups, carbamoyl groups, carboxyl groups, carbonyl groups, alkoxycarbonyl groups, halogen groups, haloalkyl groups, haloalkoxy groups, heteroayl, heterocyclic ring, arylheterocyclic ring, heterocyclic compounds, amido, imido, guanidino, hydrazido, aminoxy, alkoxyamino, alkylamido, carboxylic ester groups, thioethers groups, carboxylic acids, phosphoryl groups, polycyclic aromatic substituted with a OH, $NH_2$, SH, F, Cl, Br, I, NHR, NRR', $CN_3H_4$, a N, a O, a S, a H, or combination thereof; "X" independently comprise a C, a N, a O, a S, a H, $-CH_2-$, $-CH_2CH_2-$, $-CH=CH-$, $-C\equiv C-$, $-NH-$, $-NR-$, $-NH-NH-$, $-NH(CH_2)_nNH$, $-NR(CH_2)_nNR'-$, $-NR-NR'-$, $-NH-O-$, $-NR-O-$, $-NH(CH_2)_nO-$, $-NR(CH_2)_nO-$, $-NH(CH_2)_nS-$, $-NR(CH_2)_nS-$, $-O(CH_2)_nO-$, $-O(CH_2)_nS-$, $-S(CH_2)_nS-$, $-CO-$, $-CO_2-$, $-COS-$, $-CONH-$, $-CONR-$, $-OC(O)NH-$, $-NHCONH-$, $-CONHCO-$, $-CO(CH_2)_nCO-$, or combination thereof; "Y" independently comprise a N, a O, a C, a S or 2Hs; "n" is 0, 1, 2, 3, 4, 5, 6, 7 or more; and "A" and "B" independently comprises R1, R2, R3, R4, R'1, R'2, R'3, R'4, R"1, R"2, R"3, and R"4, an acetyl, a Boc (t-butoxycarbonyl), a Fmoc (9-fluorenylmethoxycarbonyl), a Cbz (benzyloxycarbonyl), an Aloc (allyloxycarbonyl), an amino acid, an amino acid analogue, an artificial amino acid, a peptide of 2-30 amino acids, a carbohydrate, a lipid, a nucleic acid, a sugar, a linker of 1-30 amino acids, a linker of an optionally substituted lower alkyl, a linker of an optionally substituted C1-C7 alkyl, a linker as seen below

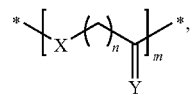

connected to a substituent (R1, R2, R3, R4, R'1, R'2, R'3, R'4, R"1, R"2, R"3, or R"4), a group, or an oligo-benzamide of the present invention.

In addition, the compositions of the instant invention may contain one or more of diluents excipients, active agents, lubricants, preservatives, stabilizers, wetting agents, emulsifiers, salts for influencing osmotic pressure, buffers, colorings, flavorings, aromatic substances, penetration enhancers, surfactants, fatty acids, bile salts, chelating agents, colloids and combinations thereof. when the instant invention is in the form of a pharmaceutical composition it may be formulated into the form of a solution, an emulsion, a liposome-containing formulation, a tablet, a capsule, a gel capsule, a liquid syrup, a soft gel, a suppository, an enema, a patch, an ointment, a lotion, a cream, a gel, a drop, a spray, a liquid or a powder.

Proteins are one of the essential components for all living organisms and are utilized to maintain and regulate nearly all critical cellular functions from intercellular communication to cell death. (T. Chittenden et al., *EMBO J* 14, 5589 (1995); P. H. Kussie et al., *Science* 274, 948 (1996).) For their actions, proteins interact with diverse molecules, and among them protein-protein complex formation is an essential theme through which many regulatory processes like modulation of enzymatic activity, signal transduction, and apoptosis, are initiated or inhibited. Therefore, small molecules that inhibit protein-protein or protein-peptide interaction have been actively pursued in an attempt to develop potential therapeutic agents.

Conventional methods for identifying such inhibitors include the preparation and screening of chemical libraries to discover lead compounds although often with little success (Cochran, A., Antagonists of protein-protein interactions. *Chem. Biol.* 2000, 7, R85-R94). This highlights a rational design approach as a compelling alternative since it can be based on a structural knowledge of the interface of protein complexes. In particular, synthetic scaffolds that mimic key elements found in the interface can potentially lead to develop potent small molecule inhibitors. (Yin, H.; Lee, G.-I.; Sedey, K. A.; Kutzki, O.; Park, H. S.; Orner, B. P.; Ernst, J. T.; Wang, H.-G.; Sebti, S. M.; Hamilton, A. D., Terphenyl-based Bak BH3 α-helical proteomimetics as low-molecular-weight antagonists of Bcl-xL. *J. Am. Chem. Soc* 2005, 127, 10191-10196.)

Among many protein secondary structures, α-helices are the most common secondary structure found in more than 40% of natural proteins, (Kabsch, W.; Sander, C., Dictionary of protein secondary structure: Pattern recognition of hydrogen-bonded and geometrical features. *Biopolymers* 1983, 22, 2577-2637) and the pharmaceutical potential for α-helix peptidomimetics is significant.

Apoptosis is essential in many physiological processes including tissue homeostasis. The B-cell lymphoma-2 (Bcl-2) and Bcl-xL are anti-apoptotic proteins whose function is regulated by the binding of pro-apoptotic factors such as Bak proteins. Bak as well as Bax, Bad, Bid and etc. is a member of the pro-apoptotic proteins and known to have the BH3 domain to interact with anti-apoptotic Bcl proteins. (Adams, J. M.; Cory, S., Life-or-death decisions by the Bcl-2 protein family. *Trends Biochem. Sci.* 2001, 26, 61-66). These protein complexes like Bcl/Bak are a key element to regulate programmed cell death. Overexpression of the anti-apoptotic proteins Bcl-2 and Bcl-xL is commonly observed in human cancers.

The binding of Bcl-xL to the 16-residue BH3 domain from Bak has been characterized by NMR. (Sattler, M.; Liang, H.; Nettesheim, D.; Meadows, R. P.; Harlan, J. E.; Eberstadt, M.; Yoon, H. S.; Shuker, S. B.; Chang, B. S.; Minn, A. J.; Thompson, C. B.; Fesik, S. W., Structure of Bcl-xL-Bak Peptide Complex: Recognition Between Regulators of Apoptosis. *Science* 1997, 275, 983-986). The NMR structure indicates that the Bak-derived peptide forms an α-helix and binds in a hydrophobic groove formed by the seven α-helices of Bcl-xL. Therefore, α-helix peptidomimetics of the BH3 domain of Bak will disrupt the interaction of Bcl-xL (or Bcl-2) and Bak (or Bax, Bad, Bid), consequently inducing cell death.

Recently, several approaches have been pursued to disrupt this Bcl/Bak protein complex formation to induce apoptosis. One approach is using stabilized α-helical peptides derived from BH3 domain developed by Walensky and coworkers. (Science 2004, 305: 1466). In addition to such peptides, many small molecules were also pursued. These small molecules include α-helix peptidomimetics using different chemical structures from the α-helix peptidomimetics of this invention. However, all of the α-helix peptidomimetics share the same goal, modulating protein-protein or protein-peptide interaction.

One embodiment provides a method of preventing the interaction between the pro-apoptotic protein Bak and the anti-apoptotic protein Bcl-xL [Kutzki, O., Park, H. S., Ernst, J. T., Orner, B. P., Yin, H. and Hamilton, A. D., J. Am. Chem. Soc., 124 (2002) 11838-11839; Yin, H., Lee, G. I., Sedey, K. A., Kutzki, O., Park, H. S., Omer, B. P., Ernst, J. T., Wang, H. G., Sebti, S. M. and Hamilton, A. D., J. Am. Chem. Soc., 127 (2005) 10191-10196.]; blocking the complex formation of the tumor-suppressor protein p53 with the oncoprotein hdm2 [Yin, H., Lee, G. I., Park, H. S., Payne, G. A., Rodriguez, J. M., Sebti, S. M. and Hamilton, A. D., Angew. Chem. Int. Ed., 44 (2005) 2704-2707.].

Figure 2:
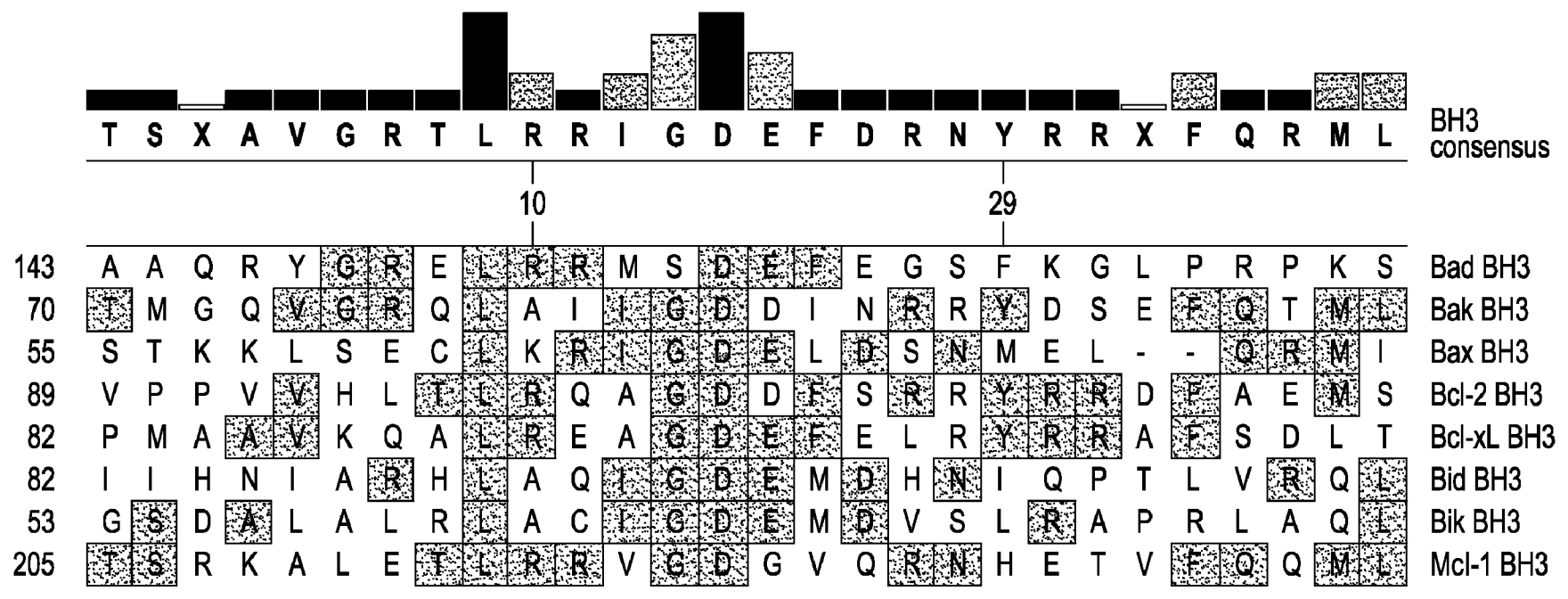

FIGS. 1A-1E are images of the structures of oligo-benzamide α-helix peptidomimetic compounds. FIG. 1A is an image of the structure of an ideal α-helix, FIG. 1B is an image of the general structure of oligo-benzamide α-helix peptidomimetic compounds, FIG. 1C is an image of the energy-minimized structure of an oligo-benzamide α-helix peptidomimetic compound, FIG. 1D is an image of the superimposition of the structures of an α-helix (green) with an oligo-benzamide α-helix peptidomimetic compound (orange), and FIG. 1E is an image of the structures of oligo-benzamide α-helix peptidomimetic compounds FIG. 1E 1, FIG. 1E 2 and FIG. 1E 3.

As seen in FIG. 1B the substitution on the oligo-benzamide structure allows the placement of three functional groups corresponding to the amino acids at the i, i+4, and i+7 positions, representing one face of a helix as can be seen in FIG. 1A. The structure of the designed α-helix peptidomimetic compounds was analyzed by molecular modeling using MacroModel (MacroModel version 9, Schrödinger, New York, N.Y.). A Monte Carlo conformational search was carried out (5,000 steps) using a MM3 force field (energy minimization was carried out using MM3 force field within MacroModel 9.0) implemented into the software. The energy-minimized structure is seen in FIG. 1C and demonstrates that the three functional groups in the peptidomimetic overlap well with the corresponding side chains of a helix seen in FIG. 1D.

The present invention provides an oligo-benzamide compound as illustrated includes 2 or 3 optionally substituted benzamides, the number of optionally substituted benzamides may be 2, 3, 4, 5, 6, 7, 8, 9, 10 or more. In addition, linkages between the optionally substituted benzamides may be varied as necessary including ester, thioester, thioamide, trans-ethylene, methylene, ethylene, methyloxy, methylamino, hydroxyethyl, carbamate, urea, imide, hydrozido, aminoxy, or other linkages known to the skilled artisan. And, the oligo-benzamide compound may be attached to amino acids, oligopeptides, optionally substituted alkyl, or other structures known to the skilled artisan.

The substitutions on the substituted benzamide are generally on a benzene ring and may be on the 2, 3, 4, 5, or 6 position of each of the benzene rings. The substitutions may be at the same position on each of the benzene rings but may also be at different positions on each of the benzene rings. The one or more substitutions may include any necessary functional groups to achieve the desired effect. For example, the one or more substitutions are connected to the benzamide ring by a chemical linkage including ether, thioether, amine, amide, carbamate, urea, and carbon-carbon (single, double, and triple) bonds, and the one or more substitutions comprise one or more optionally substituted alkyl groups, lower alkyl groups, alkoxy groups, alkoxyalkyl groups, hydroxy groups, hydroxyalkyl groups, alkenyl groups, amino groups, imino groups, nitrate groups, alkylamino groups, nitroso groups, aryl groups, biaryl groups, bridged aryl groups, fused aryl groups, alkylaryl groups, arylalkyl groups, arylalkoxy groups, arylalkylamino groups, cycloalkyl groups, bridged cycloalkyl groups, cycloalkoxy groups, cycloalkyl-alkyl groups, arylthio groups, alkylthio groups, alkylsulfinyl groups, alkylsulfonyl groups, arylsulfonyl groups, arylsulfinyl groups, caboxamido groups, carbamoyl groups, carboxyl groups, carbonyl groups, alkoxycarbonyl groups, halogen groups, haloalkyl groups, haloalkoxy groups, heteroayl, heterocyclic ring, arylheterocyclic ring, heterocyclic compounds, amido, imido, guanidino, hydrazido, aminoxy, alkoxyamino, alkylamido, carboxylic ester groups, thioethers groups, carboxylic acids, phosphoryl groups or combination thereof.

The present invention also provides an oligo-benzamide compound that includes at least two optionally substituted benzamides, with each of the substituted benzamides having one or more substitutions on a benzene ring. The one or more substitutions are individually attached to the benzene rings of the oligo-benzamide compound by a chemical linkage including ether, thioether, amine, amide, carbamate, urea, and carbon-carbon (single, double, and triple) bonds. The one or more substitutions generally include one or more optionally substituted alkyl groups, lower alkyl groups, alkoxy groups, alkoxyalkyl groups, hydroxy groups, hydroxyalkyl groups, alkenyl groups, amino groups, imino groups, nitrate groups, alkylamino groups, nitroso groups, aryl groups, biaryl groups, bridged aryl groups, fused aryl groups, alkylaryl groups, arylalkyl groups, arylalkoxy groups, arylalkylamino groups, cycloalkyl groups, bridged cycloalkyl groups, cycloalkoxy groups, cycloalkyl-alkyl groups, arylthio groups, alkylthio groups, alkylsulfinyl groups, alkylsulfonyl groups, arylsulfonyl groups, arylsulfinyl groups, caboxamido groups, carbamoyl groups, carboxyl groups, carbonyl groups, alkoxycarbonyl groups, halogen groups, haloalkyl groups, haloalkoxy groups, heteroayl, heterocyclic ring, arylheterocyclic ring, heterocyclic compounds, amido, imido, guanidino, hydrazido, aminoxy, alkoxyamino, alkylamido, carboxylic ester groups, thioethers groups, carboxylic acids, phosphoryl groups or combination thereof.

The substitutions may be on a single first face of the oligo-benzamide compound to form an oligo-benzamide α-helix peptidomimetic compound or on two faces of the oligo-benzamide compound to form an oligo-benzamide amphiphilic α-helix peptidomimetic compound.

A third optionally substituted benzamide with one or more optional substitutions on a benzene ring may be connected to one of the at least two optionally substituted benzamides. When an oligo-benzamide compound has one or more substitutions on its single first face, one or more substituents correspond to an i position, i+3 position or an i+4 position, and an i+7 position of a target peptide or protein. The present invention also provides an oligo-benzamide compound having one or more substitutions on a first face and a second face of the oligo-benzamide compound, wherein an oligo-benzamide amphiphilic α-helix peptidomimetic is formed as illustrated in FIG. 6. The one or more substitutions are at one or more positions of the oligo-benzamide selected from an i position, an i+2 position, an i+3 position, an i+4 position, an i+5 position, and an i+7 position of a target peptide or protein.

The present invention includes both methods of treatment and pharmaceutical composition includes a therapeutically effective amount of an oligo-benzamide compound or a salt, a solvent, or a derivative thereof based on an oligo-benzamide compound, and one or more pharmaceutically acceptable carriers. For example, the tris-benzamide compound includes three optionally substituted benzamides and one or more substituted groups attached to each of the substituted benzamides individually by a chemical linkage including ether, thioether, amine, amide, carbamate, urea, and carbon-carbon (e.g., single, double, and triple) bonds. The pharmaceutical composition may also include one or more additional active ingredients, diluents, excipients, active agents, lubricants, preservatives, stabilizers, wetting agents, emulsifiers, salts for influencing osmotic pressure, buffers, colorings, flavorings, aromatic substances, penetration enhancers, surfactants, fatty acids, bile salts, chelating agents, colloids and combinations thereof. The pharmaceutical compound may be adapted for oral, dermatological, transdermal or parenteral administration, in the form of a solution, a emulsions, a liposome-containing formulation, a tablet, a capsule, a gel capsule, a liquid syrup, a soft gel, a suppository, an enema, a patch, an ointment, a lotion, a cream, a gel, a drop, a spray, a liquid or a powder.

The present invention provides compounds having the general formulas:

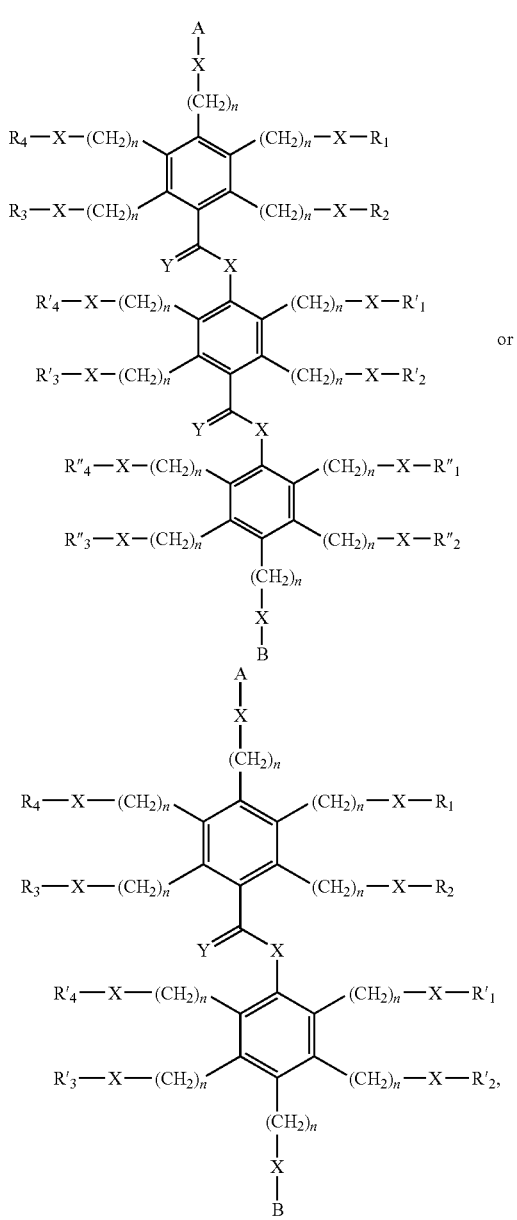

wherein each of the formulas may be substituted as follows. X may independently be a C, a N, a O, a S, a H, —CH$_2$—, —CH$_2$CH$_2$—, —CH=CH—, —C≡C—, —NH—, —NR—, —NH—NH—, —NH(CH$_2$)$_n$NH, —NR(CH$_2$)$_n$NR'— —NR—NR'—, —NH—O—, —NR—O—, —NH (CH₂)ₙO—, —NR(CH₂)ₙO—, —NH(CH₂)ₙS—, —NR(CH₂)ₙS—, —O(CH₂)ₙO—, —O(CH₂)ₙS—, —S(CH₂)ₙS—, —CO—, —CO₂—, —COS—, —CONH—, —CONR—, —OC(O)NH—, —NHCONH—, —CONHCO—, —CO(CH₂)ₙCO—, or combination thereof; and Y may be independently a N, a O, a S or 2 H's. And, n is 0, 1, 2, 3, 4, 5, 6, 7 etc.

R1, R2, R3, R4, R'1, R'2, R'3, R'4, R"1, R"2, R"3, and R"4, comprise independently a H, optionally substituted alkyl, lower alkyl, alkoxy, alkoxyalkyl, hydroxy, hydroxyalkyl, alkenyl, amino, imino, nitrate, alkylamino, dialkylamino, nitro, nitroso, aryl, biaryl, polycyclic aromatic, alkylaryl, arylalkyl, arylalkoxy, arylalkylamino, cycloalkyl, bridged cycloalkyl, cycloalkoxy, cycloalkyl-alkyl, arylthio, alkylthio, alkylsulfinyl, alkylsulfonyl, arylsulfonyl, arylsulfinyl, caboxamido, carbamoyl, carboxyl, carbonyl, alkoxycarbonyl, halogen, haloalkyl, haloalkoxy, heteroayl, heterocyclic ring, arylheterocyclic ring, heterocyclic compounds, amido, imido, guanidino, hydrazido, aminoxy, alkoxyamino, alkylamido, urea, carboxylic ester, thioether, carboxylic acid, phosphoryl groups, polycyclic aromatic substituted with a OH, NH₂, SH, F, Cl, Br, I, NHR, NRR', CN₃H₄, a N, a O, a S, a H, or combination thereof.

Alternatively, R1, R2, R3, R4, R'1, R'2, R'3, R'4, R"1, R"2, R"3, and R"4 may be one or more of the following:

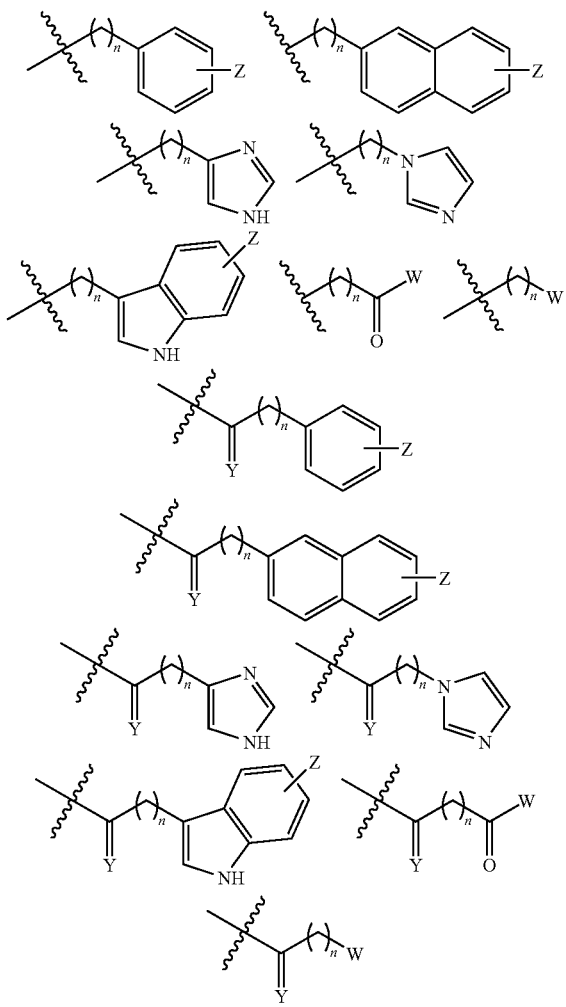

where Z is an OH, NH₂, SH, F, Cl, Br, I. W is an OH, an OR, a NH₂, a NHR, a NRR'(R, R' are alkyl groups), and an imine (C(NH)R₁R₂. For example, when R1 is a NH₂ and R₂ is a NH the imine is actually a guanidine group), and n is 0, 1, 2, 3, 4, 5, 6, 7 etc.

"A" may be a substituent (R1, R2, R3, R4, R'1, R'2, R'3, R'4, R"1, R"2, R"3, or R"4), an acetyl, a Boc (t-butoxycarbonyl), a Fmoc (9-fluorenylmethoxycarbonyl), a Cbz (benzyloxycarbonyl), an Aloc (allyloxycarbonyl), an alkyl group, an alanine, an arginine, an asparagine, an aspartic acid, a cysteine, a glutamic acid, a glutamine, a glycine, a histidine, an isoleucine, a leucine, a lysine, a methionine, a phenylalanine, a proline, a serine, a threonine, a tryptophan, a tyrosine, or a valine. "A" may be a peptide. For example, "A" may be a peptide (including a dipeptide, tripeptide, tetrapeptide, pentapeptide, or an oligopeptide consists of no greater than 50 amino acids) which has greater than 50% sequence homology to a portion of the Bad, Bak, Bax, Bcl-2, Bcl-xL, Bid, Bik, or Mcl-1 protein.

In addition "A" may be a linker as seen below

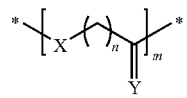

connected to a substituent (R1, R2, R3, R4, R'1, R'2, R'3, R'4, R"1, R"2, R"3, or R"4), an alanine, an arginine, an asparagine, an aspartic acid, a cysteine, a glutamic acid, a glutamine, a glycine, a histidine, an isoleucine, a leucine, a lysine, a methionine, a phenylalanine, a proline, a serine, a threonine, a tryptophan, a tyrosine, a valine, a dipeptide, a tripeptide, a tetrapeptide, a pentapeptide, or an oligopeptide.

"B" may be a substituent (R1, R2, R3, R4, R'1, R'2, R'3, R'4, R"1, R"2, R"3, R"4), an alanine, an arginine, an asparagine, an aspartic acid, a cysteine, a glutamic acid, a glutamine, a glycine, a histidine, an isoleucine, a leucine, a lysine, a methionine, a phenylalanine, a proline, a serine, a threonine, a tryptophan, a tyrosine, a valine, an alkyl group, dipeptide, tripeptide, tetrapeptide, pentapeptide, or oligopeptide. "B" may be a peptide. For example, "B" may be a peptide (including a dipeptide, tripeptide, tetrapeptide, pentapeptide, or an oligopeptide consists of no greater than 50 amino acids) which has greater than 50% sequence homology to a portion of the Bad, Bak, Bax, Bcl-2, Bcl-xL, Bid, Bik, or Mcl-1 protein. In addition "B" may be a linker as seen below

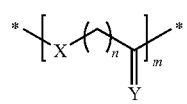

connected to a substituent (R1, R2, R3, R4, R'1, R'2, R'3, R'4, R"1, R"2, R"3, or R"4), an alkyl group, or one or more compounds disclosed herein, e.g., a second oligo-benzamide.

The present invention provides compounds having the general formulas:

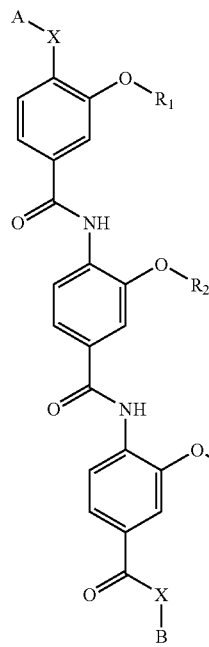
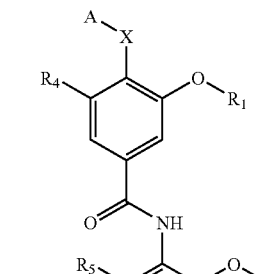
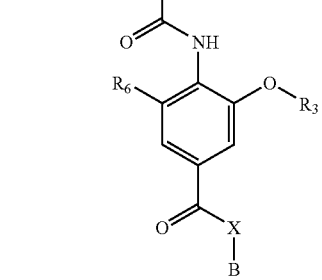

or

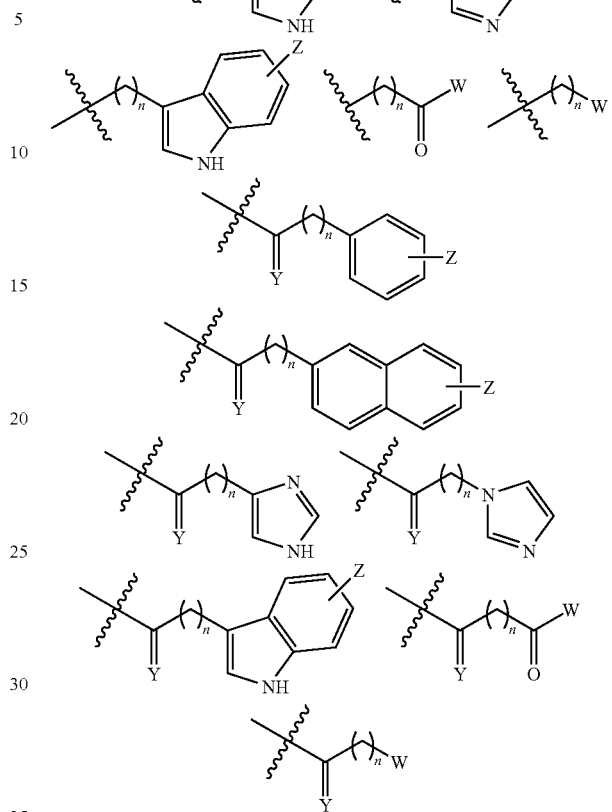

wherein each of the formulas may be substituted as follows. X may independently be a C, a N, a O, a S, a H, —CH$_2$—, —CH$_2$CH$_2$—, —CH═CH—, —C≡C—, —NH—, —NR—, —NH—NH—, —NH(CH$_2$)$_n$NH, —NR(CH$_2$)$_n$NR'—, —NR—NR'—, —NH—O—, —NR—O—, —NH(CH$_2$)$_n$O—, —NR(CH$_2$)$_n$O—, —NH(CH$_2$)$_n$S—, —NR(CH$_2$)$_n$S—, —O(CH$_2$)$_n$O—, —O(CH$_2$)$_n$S—, —S(CH$_2$)$_n$S—, —CO—, —CO$_2$—, —COS—, —CONH—, —CONR—, —OC(O)NH—, —NHCONH—, —CONHCO—, —CO(CH$_2$)$_n$CO—, or combination thereof; and Y may be independently a N, a O, a S or 2 H's. And, n is 0, 1, 2, 3, 4, 5, 6, 7 etc.

R1, R2, R3, R4, R5, and R6 independently comprise a H, optionally substituted alkyl, lower alkyl, alkoxy, alkoxyalkyl, hydroxy, hydroxyalkyl, alkenyl, amino, imino, nitrate, alkylamino, dialkylamino, nitro, nitroso, aryl, biaryl, polycyclic aromatic, alkylaryl, arylalkyl, arylalkoxy, arylalkylamino, cycloalkyl, bridged cycloalkyl, cycloalkoxy, cycloalkylalkyl, arylthio, alkylthio, alkylsulfinyl, alkylsulfonyl, arylsulfonyl, arylsulfinyl, caboxamido, carbamoyl, carboxyl, carbonyl, alkoxycarbonyl, halogen, haloalkyl, haloalkoxy, heteroayl, heterocyclic ring, arylheterocyclic ring, heterocyclic compounds, amido, imido, guanidino, hydrazido, aminoxy, alkoxyamino, alkylamido, urea, carboxylic ester, thioether, carboxylic acid, phosphoryl groups, polycyclic aromatic substituted with a OH, NH$_2$, SH, F, Cl, Br, I, NHR, NRR', CN$_3$H$_4$, a N, a O, a S, a H, or combination thereof.

Alternatively, R1, R2, R3, R4, R5, and R6 may be one or more of the following:

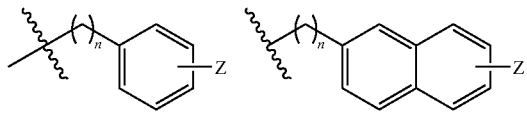

where Z is an OH, NH$_2$, SH, F, Cl, Br, I. W is an OH, an OR, a NH$_2$, a NHR, a NRR'(R, R' are alkyl groups), and an imine (C(NH)R$_1$R$_2$. For example, when R1 is a NH$_2$ and R$_2$ is a NH the imine is actually a guanidine group), and n is 0, 1, 2, 3, 4, 5, 6, 7 etc.

"A" may be a substituent (R1, R2, R3, R4, R5, R6, R'1, R'2, R'3, R'4, R"1, R"2, R"3, or R"4), an acetyl, a Boc (t-butoxycarbonyl), a Fmoc (9-fluorenylmethoxycarbonyl), a Cbz (benzyloxycarbonyl), an Aloc (allyloxycarbonyl), an alkyl group, an alanine, an arginine, an asparagine, an aspartic acid, a cysteine, a glutamic acid, a glutamine, a glycine, a histidine, an isoleucine, a leucine, a lysine, a methionine, a phenylalanine, a proline, a serine, a threonine, a tryptophan, a tyrosine, a valine, a dipeptide, a tripeptide, a tetrapeptide, a pentapeptide, or an oligopeptide.

In addition "A" may be a linker as seen below

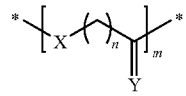

connected to a substituent (R1, R2, R3, R4, R5 or R6), an alanine, an arginine, an asparagine, an aspartic acid, a cysteine, a glutamic acid, a glutamine, a glycine, a histidine, an isoleucine, a leucine, a lysine, a methionine, a phenylalanine, a proline, a serine, a threonine, a tryptophan, a tyrosine, a valine, a dipeptide, a tripeptide, a tetrapeptide, a pentapeptide, or an oligopeptide consists of no greater than 50 amino acids) which has greater than 50% sequence homology to a portion of the Bad, Bak, Bax, Bcl-2, Bcl-xL, Bid, Bik, or Mcl-1 protein.

"B" may be a substituent (R1, R2, R3, R4, R5, or R6), an alanine, an arginine, an asparagine, an aspartic acid, a cysteine, a glutamic acid, a glutamine, a glycine, a histidine, an isoleucine, a leucine, a lysine, a methionine, a phenylalanine, a proline, a serine, a threonine, a tryptophan, a tyrosine, a valine, an alkyl group, a dipeptide, a tripeptide, a tetrapeptide, a pentapeptide, or an oligopeptide. "B" may be a peptide. For example, "B" may be a peptide (including a dipeptide, tripeptide, tetrapeptide, pentapeptide, or an oligopeptide consists of no greater than 50 amino acids) which has greater than 50% sequence homology to a portion of the Bad, Bak, Bax, Bcl-2, Bcl-xL, Bid, Bik, or Mcl-1 protein. In addition "B" may be a linker as seen below

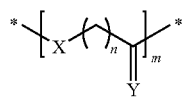

connected to a substituent (R1, R2, R3, R4, R5, or R6), an optionally substituted alkyl, lower alkyl, alkoxy, alkoxyalkyl, hydroxy, hydroxyalkyl, alkenyl, amino, imino, nitrate, alkylamino, dialkylamino, nitro, nitroso, aryl, biaryl, polycyclic aromatic, alkylaryl, arylalkyl, arylalkoxy, arylalkylamino, cycloalkyl, bridged cycloalkyl, cycloalkoxy, cycloalkylalkyl, arylthio, alkylthio, alkylsulfinyl, alkylsulfonyl, arylsulfonyl, arylsulfinyl, caboxamido, carbamoyl, carboxyl, carbonyl, alkoxycarbonyl, halogen, haloalkyl, haloalkoxy, heteroayl, heterocyclic ring, arylheterocyclic ring, heterocyclic compounds, amido, imido, guanidino, hydrazido, aminoxy, alkoxyamino, alkylamido, urea, carboxylic ester, thioether, carboxylic acid, phosphoryl groups, polycyclic aromatic substituted with a OH, $NH_2$, SH, F, Cl, Br, I, NHR, NRR', $CN_3H_4$, a N, a O, a S, a H, one or more oligo-benzamide of the present invention or combination thereof.

The present invention provides an oligo-benzamide compound having the formula:

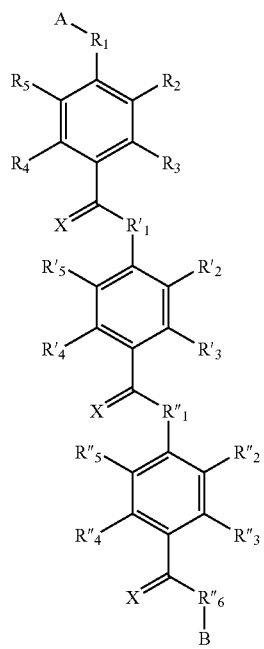

wherein R2, R3, R4, R5, R'2, R'3, R'4, R'5, R"2, R"3, R"4, and R"5 independently comprise a H, one or more optionally substituted alkyl groups, lower alkyl groups, alkoxy groups, alkoxyalkyl groups, hydroxy groups, hydroxyalkyl groups, alkenyl groups, amino groups, imino groups, nitrate groups, alkylamino groups, nitroso groups, aryl groups, biaryl groups, bridged aryl groups, fused aryl groups, alkylaryl groups, arylalkyl groups, arylalkoxy groups, arylalkylamino groups, cycloalkyl groups, bridged cycloalkyl groups, cycloalkoxy groups, cycloalkyl-alkyl groups, arylthio groups, alkylthio groups, alkylsulfinyl groups, alkylsulfonyl groups, arylsulfonyl groups, arylsulfinyl groups, caboxamido groups, carbamoyl groups, urea groups, carboxyl groups, carbonyl groups, alkoxycarbonyl groups, halogen groups, haloalkyl groups, haloalkoxy groups, heteroayl, heterocyclic ring, arylheterocyclic ring, heterocyclic compounds, amido, imido, guanidino, hydrazido, aminoxy, alkoxyamino, alkylamido, carboxylic ester groups, thioethers groups, carboxylic acids, phosphoryl groups or combination thereof; R1, R'1, R"1 independently comprise a C, a N, a O, a S, a H, —$CH_2$—, —$CH_2CH_2$—, —CH=CH—, —C≡C—, —NH—, —NR—, —NH—NH—, —$NH(CH_2)_nNH$, —$NR(CH_2)_nNR'$— —NR—NR'—, —NH—O—, —NR—O—, —NH$(CH_2)_nO$—, —$NR(CH_2)_nO$—, —$NH(CH_2)_nS$—, —NR$(CH_2)_nS$—, —O$(CH_2)_nO$—, —O$(CH_2)_nS$—, —S$(CH_2)_n$S—, —CO—, —$CO_2$—, —COS—, —CONH—, —CONR—, —OC(O)NH—, —NHCONH—, —CONHCO—, —CO$(CH_2)_n$CO—, or combination thereof; X comprises a N, a O, a S or 2 Hs; R"6 comprises a C, a N, a O, a S, a H, —$CH_2$—, —$CH_2CH_2$—, —CH=CH—, —C≡C—, —NH—, —NR—, —NH—NH—, —$NH(CH_2)_nNH$, —NR$(CH_2)_nNR'$— —NR—NR'—, —NH—O—, —NR—O—, —NH$(CH_2)_nO$—, —NR$(CH_2)_nO$—, —NH$(CH_2)_nS$—, —NR$(CH_2)_nS$—, —O$(CH_2)_nO$—, —O$(CH_2)_nS$—, —S$(CH_2)_nS$—, —CO—, —$CO_2$—, —COS—, —CONH—, —CONR—, —OC(O)NH—, —NHCONH—, —CONHCO—, —CO$(CH_2)_nCO$—, or combination thereof; "A" comprises an acetyl, Boc, 9-fluorenylmethyl carbamate, Cbz, Aloc, an amino acid, an amino acid analogue, an artificial amino acid, a dipeptide, a tripeptide, a tetrapeptide, a pentapeptide, a peptide sequence of between 2 and 30 amino acids, a linker of 1-20 amino acids, a linker of an optionally substituted lower alkyl, a linker of an optionally substituted C1-C7 alkyl or a combination thereof; and "B" comprises an optionally substituted lower alkyl, an optionally substituted C1-C7 alkyl, an amino acid, an amino acid analogue, an artificial amino acid, a dipeptide, a tripeptide, a tetrapeptide, or a pentapeptide; a peptide sequence of between 2 and 30 amino acids; a linker of 1-20 amino acids, C1-C7 alkyl or combination thereof, which may also be connected to one or more optionally substituted alkyl, lower alkyl, alkoxy, alkoxyalkyl, hydroxy, hydroxyalkyl, alkenyl, amino, imino, nitrate, alkylamino, dialkylamino, nitro, nitroso, aryl, biaryl, polycyclic aromatic, alkylaryl, arylalkyl, arylalkoxy, arylalkylamino, cycloalkyl, bridged cycloalkyl, cycloalkoxy, cycloalkyl-alkyl, arylthio, alkylthio, alkylsulfinyl, alkylsulfonyl, arylsulfonyl, arylsulfinyl, caboxamido, carbamoyl, carboxyl, carbonyl, alkoxycarbonyl, halogen, haloalkyl, haloalkoxy, heteroayl, heterocyclic ring, arylheterocyclic ring, heterocyclic compounds, amido, imido, guanidino, hydrazido, aminoxy, alkoxyamino, alkylamido, urea, carboxylic ester, thioether, carboxylic acid, phosphoryl groups, polycyclic aromatic substituted with a OH, $NH_2$, SH, F, Cl, Br, I, NHR, NRR', $CN_3H_4$, a N, a O, a S, a H, one or more oligo-benzamide of the present invention or combination thereof.

One example includes a compound having the formula:

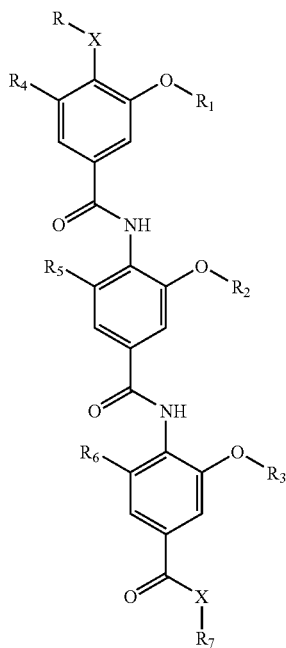

wherein R, R1, R2, R3, R4, R5, R6 and R7 individually comprise a C, a N, a O, a S, a H, one or more optionally substituted alkyl groups, lower alkyl groups, alkoxy groups, alkoxyalkyl groups, hydroxy groups, hydroxyalkyl groups, alkenyl groups, amino groups, imino groups, nitrate groups, alkylamino groups, nitroso groups, aryl groups, biaryl groups, bridged aryl groups, fused aryl groups, alkylaryl groups, arylalkyl groups, arylalkoxy groups, arylalkylamino groups, cycloalkyl groups, bridged cycloalkyl groups, cycloalkoxy groups, cycloalkyl-alkyl groups, arylthio groups, alkylthio groups, alkylsulfinyl groups, alkylsulfonyl groups, arylsulfonyl groups, arylsulfinyl groups, caboxamido groups, carbamoyl groups, carboxyl groups, carbonyl groups, alkoxycarbonyl groups, halogen groups, haloalkyl groups, haloalkoxy groups, heteroayl, heterocyclic ring, arylheterocyclic ring, heterocyclic compounds, amido, imido, guanidino, hydrazido, aminoxy, alkoxyamino, alkylamido, urea groups, carboxylic ester groups, thioethers groups, carboxylic acids, phosphoryl groups or combination thereof, an acetyl, a Boc (t-butoxycarbonyl), a Fmoc (9-fluorenylmethoxycarbonyl), a Cbz (benzyloxycarbonyl), an Aloc (allyloxycarbonyl), an amino acid, an amino acid analogue, an artificial amino acid, a dipeptide, a tripeptide, a tetrapeptide, a pentapeptide, a linker of 1-20 amino acids, a linker of an optionally substituted lower alkyl, a linker of an optionally substituted C1-C7 alkyl, a polycyclic aromatic substituted with a OH, a $NH_2$, a SH, a F, a Cl, a Br, a I, a NHR, a NRR', a guanidine ($CN_3H_4$), a N, a O, a S, a H, a peptide sequence of between 2 and 30 amino acids, a linker of 1-20 amino acids, an optionally substituted C1-C7 alkyl or a combination thereof, which may also be connected to one or more compounds.

FIG. 2 is a sequence comparison of various BH3 domains. To explore the therapeutic potential, the α-helix peptidomimetic compounds of various BH3 domains were examined for their effect on various tumor cells including prostate cancer cells. The present invention provides synthetic molecules which present the essential functionalities of corresponding peptides in the proper three dimensional orientation that enables specific protein interactions, leading to either stimulation or inhibition of protein-mediated functions. FIG. 2 is a comparison of the sequence of the BH3 domain from Bad, Bak, Bax, Bcl-2, Bcl-xL, Bid, Bik, and Mcl-1 proteins. The amino acid sequence is shown for each is compared and a consensus sequence is provided for the BH3 domain.

The present invention provides a synthesis scheme to prepare α-helix mimetic compounds of the present invention. For example, a number of α-helix mimetic compounds were made starting with a 4-amino-3-hydroxybenzoic acid compound, which was converted to an N-Ac protected methyl ester compound. Various alkyl groups were introduced to the hydroxyl group using a variety of alkyl halides and a base (e.g., NaH, NaOMe) known to the skilled artisan. After the alkylation reaction, the methyl ester compound 9 was hydrolyzed using a base (e.g., LiOH), and methyl 4-amino-3-hydroxybenzoate compound was coupled to the free benzoic acid using a coupling reagent (e.g., BOP), resulting in a bis-benzamide compound containing one alkyl group corresponding to the i position of a helix. These steps were repeated to synthesize oligo-benzamide compounds.

FIG. 3 is a scheme for the synthesis of two tris-benzamides 8A and 8B, where tris-benzamides 8A includes a R1 that is an acetyl (Ac) group, R2 is a benzyl (Bn) group and R3 and R4 are 4-fluorobenzyl groups and tris-benzamides 8B includes a R1 is a t-butoxycarbonyl (Boc) group, R2 is a methyl (Me) group and R3 is a benzyl (Bn) group and R4 is a 2-naphthylmethyl group. After the alkylation of the hydroxybenzoate compound, the methyl ester 10 was hydrolyzed using NaOH, and methyl 4-amino-3-hydroxybenzoate was coupled to the benzoic acid (compound 12A where R1 is an acetyl (Ac) group and R2 as a benzyl (Bn) group and compound 12B where R1 as a t-butyloxycarbonyl (Boc) group and R2 as a methyl (Me) group) using thionyl chloride, resulting in a bis-benzamide containing one alkyl group corresponding to the i position of a helix (compound 14A where R1 as an acetyl (Ac) group and R2 as a benzyl (Bn) group and compound 14B where R1 as a t-butyloxycarbonyl (Boc) group and R2 as a methyl (Me) group). The alkylation and coupling reactions were repeated twice to place two other functional groups corresponding to the i+4 (or i+3) and i+7 positions as seen in compound 16A where R1 is an acetyl (Ac) group, R2 is a benzyl (Bn) group and R3 is a 4-fluorobenzyl group; compound 16B where R1 is a t-butyloxycarbonyl (Boc) group, R2 is a methyl (Me) group and R3 is a benzyl (Bn) group; compound 18A where R1 is an acetyl (Ac) group, R2 is a benzyl (Bn) group and R3 is a 4-fluorobenzyl group; compound 18B where R1 is a t-butoxycarbonyl (Boc) group, R2 is a methyl (Me) group and R3 is a benzyl (Bn) group; tris-benzamides 8A where R1 is an acetyl (Ac) group, R2 is a benzyl (Bn) group and R3 and R4 are 4-fluorobenzyl groups; and tris-benzamides 8B where R1 is a t-butoxycarbonyl (Boc) group, R2 is a methyl (Me) group and R3 is a benzyl (Bn) group and R4 is a 2-naphthylmethyl group.

Figure 4A:
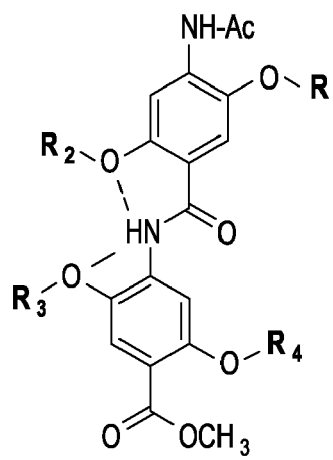
FIG. 4A is an image of a bis-benzamide structure that is used to generate α-helix peptidomimetic compounds of the present invention.
Figure 4B:
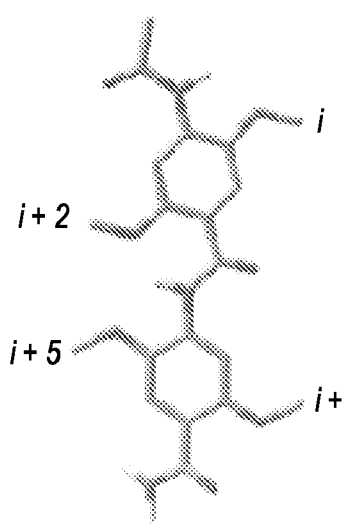
FIGS. 4B and 4C are images of the energy-minimized structure of a bis-benzamide α-helix peptidomimetic compound.

The present invention also provides an amphiphilic α-helix peptidomimetic using a different template. The template used to mimic an amphiphilic α-helix, is a bis-benzamide structure that constitutes two 4-amino-2,5-dihydroxybenzoic acid moieties as seen in FIGS. 4A and 4B. Analogous to the building block of the original amphiphilic α-helix peptidomimetic (3,4-diamino-5-hydroxybenzoic acid in FIG. 6A), the building block of the alternative scaffold (4-amino-2,5-dihydroxybenzoic acid) also has two hydroxyl groups at the 2- and 5-positions to present two functional groups found on opposite faces of an α-helix. However, the structure of the alternative scaffold is quite different compared to the original one. Its structure was also analyzed by molecular modeling using MacroModel (a Monte Carlo conformational search).

Figure 4C:
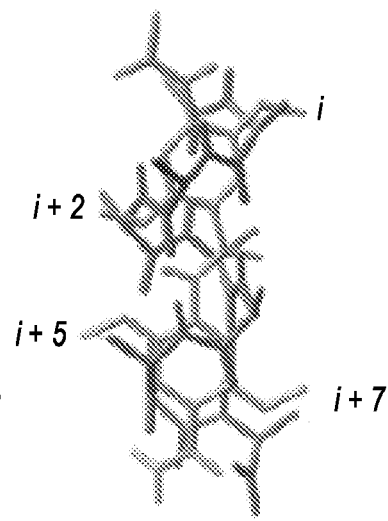

FIG. 4C is an image of the energy minimized structure of the lowest energy conformation was analyzed by molecular modeling using MacroModel. The energy minimized structure of the lowest energy conformation showed significantly enhanced rigidity in the structure, resulting from two hydrogen bonds made by the benzamide proton and two nearby alkoxy groups (R2 and R3), one from the 2-position in the upper benzene ring and the other from the 5-position in the lower benzene ring. These hydrogen bonds tightly secure the relative orientation of two benzene rings, and direct two alkyl groups (R2 and R3) at the 2-position in the upper ring and the 5-position in the lower ring on the same side of the structure. This results in the remaining two alkyl groups (R1 and R4) at the 5-position in the upper ring and the 2-position in the lower ring being on the same side, opposite to the former two groups (R2 and R3). Superimposition of this alternative amphiphilic α-helix peptidomimetic over an α-helix reveals that 4 alkyl groups (R1-4) in the peptidomimetic represent 4 side chains of the helix extremely well as seen in FIG. 4C. The hydrogen bonds increase the distance between two alkyl groups (R1 and R4) at the 5-position in the upper ring and the 2-position in the lower ring, well representing the i and i+7 positions. On the other hand, the two alkyl groups (R2 and R3) being in close proximity due to the hydrogen bonds overlay well to the side chain groups at the i+2 and i+5 positions on the opposite face of a helix.

Figure 5:
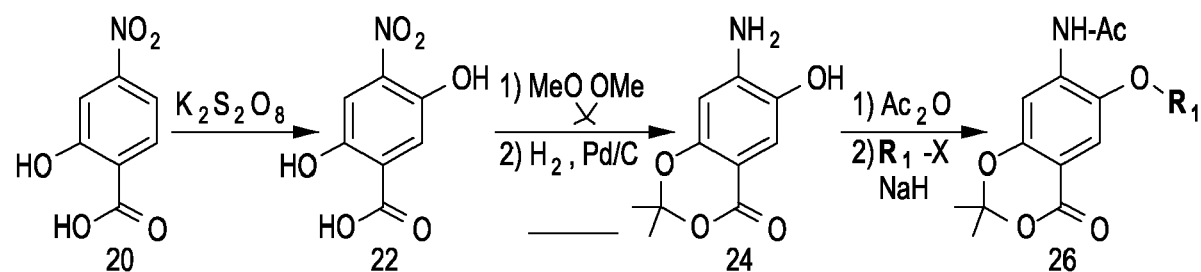
FIG. 5 is a scheme for the synthesis of bis-benzamide α-helix peptidomimetic compounds of the present invention.
Figure 5:
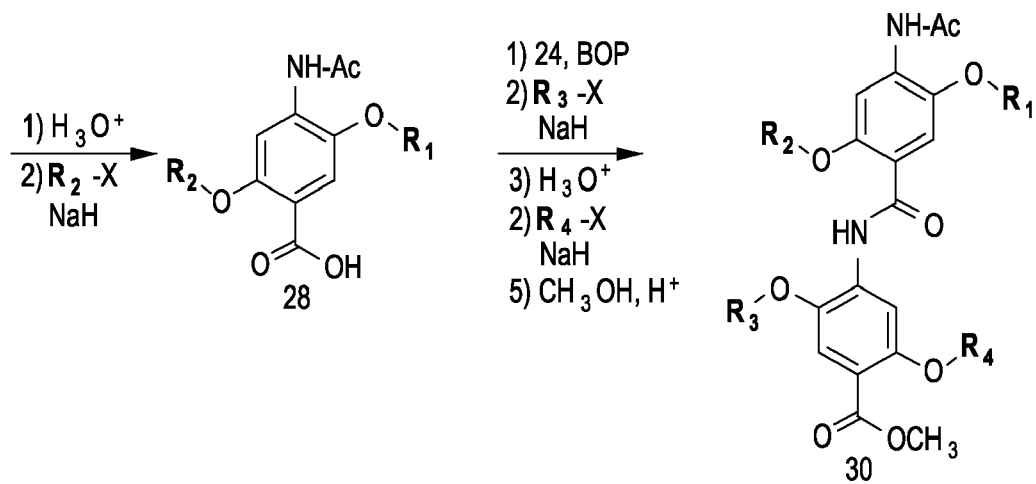

FIG. 5 is a scheme for the synthesis of the alternative amphiphilic α-helix peptidomimetics of the present invention. The 4-nitrosalicylic acid compound 20 was oxidized with persulfate. The Boyland-Sim oxidation reaction produced 4-nitro-2,5-dihydroxybenzoic acid compound 22, and the 1-carboxy and 2-hydroxyl groups were protected as a ketal by the treatment of 2,2-dimethoxypropane and the 4-nitro group was reduced by hydrogenation to yield the 4-amino compound 24. After the 4-amino group of the building block compound was acetylated, an alkyl group (R1) was introduced to the free 5-hydroxyl group using various alkyl halides and a base (NaH or NaOMe) for the side chain functionality at the i position. Subsequently, the ketal was removed by an acidic treatment and a second alkylation reaction was carried out to place a functional group (R2) for the i+2 position. The second building block (compound 24) was coupled using BOP or PyBrOP to form a bis-benzamide. The steps (alkylation, deprotection, and another alkylation) were repeated to prepare the compound 30.

Figure 6C:
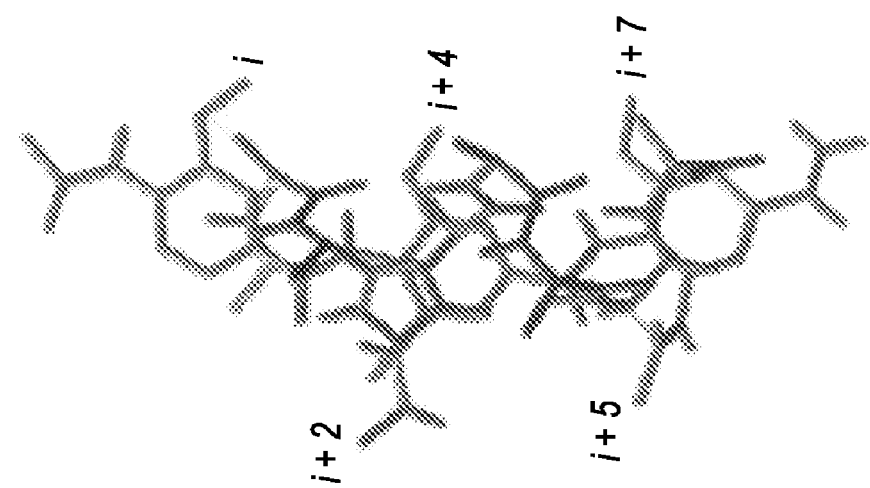
FIGS. 6A-6C are images that illustrate the structures of oligo-benzamide α-helix peptidomimetic compounds that represent two α-helical faces of a peptide or protein.
Figure 6B:
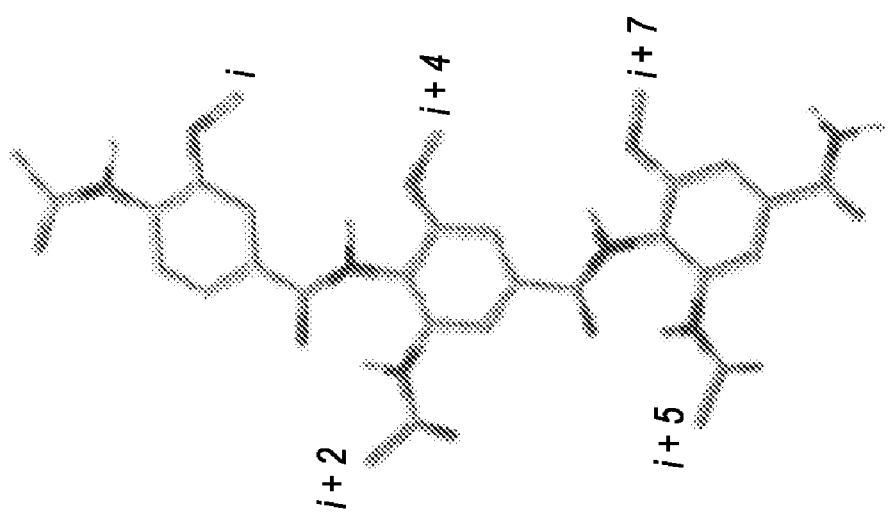
Figure 6A:
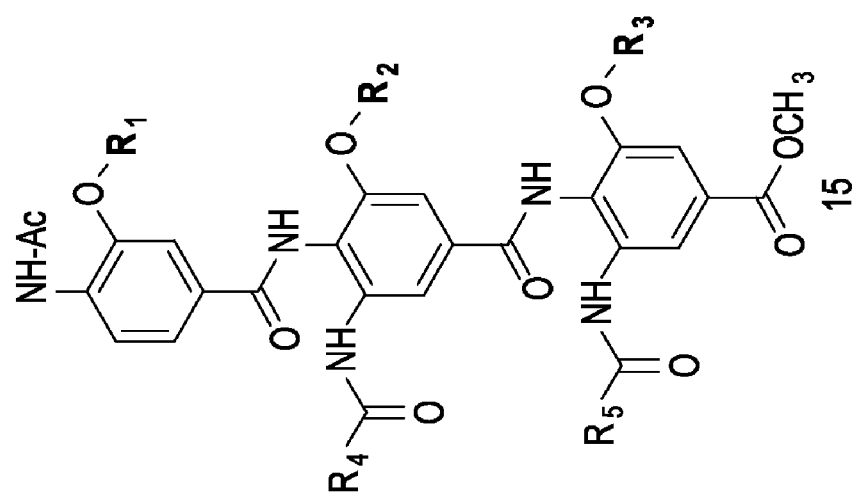

FIG. 6A is an image of oligo-benzamide compound having one or more substitutions on a first face and a second face of the oligo-benzamide compound, to form the amphiphilic α-helix peptidomimetic compounds of the present invention. The one or more substitutions are at one or more positions of the oligo-benzamide selected from an i position, an i+2 position, an i+3 position, an i+4 position, an i+5 position, and an i+7 position of a target peptide or protein. FIGS. 6B and 6C are images of the energy minimized structures of a oligo-benzamide α-helix peptidomimetic compound that represents the two α-helical faces of a peptide or protein.

Figure 7:
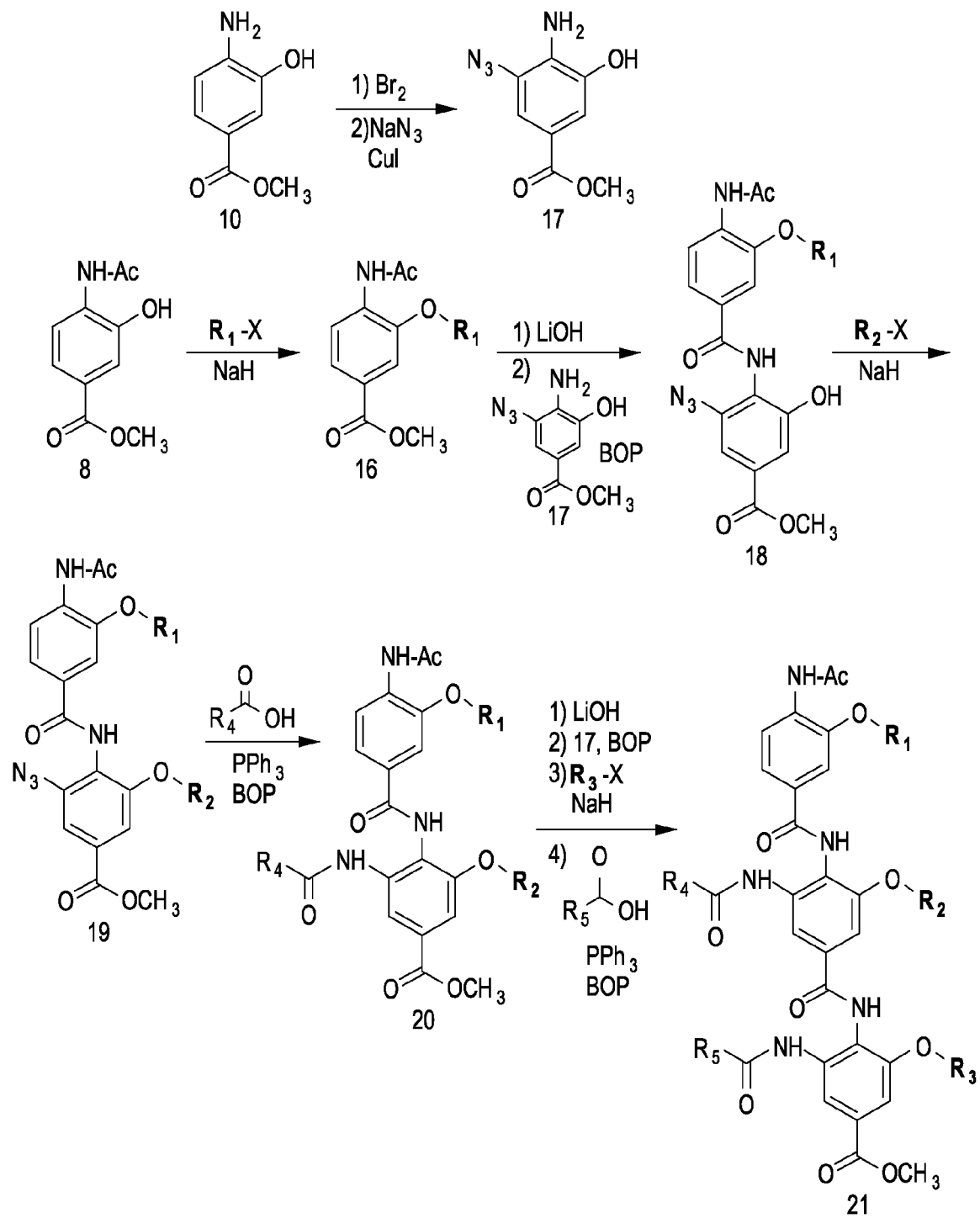
FIG. 7 is a scheme for the synthesis of oligo-benzamide peptidomimetic compounds that represent two α-helical faces of a peptide or protein.
Figure 8A:
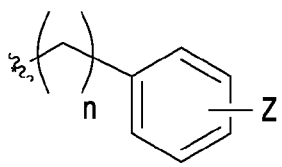
FIGS. 8A-8N are images of various structures of substituted groups that may be placed at the R positions of the oligo-benzamide α-helix peptidomimetic compounds.
Figure 8B:
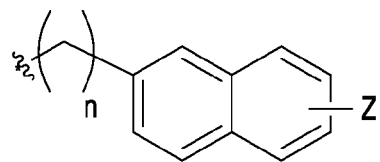
Figure 8C:
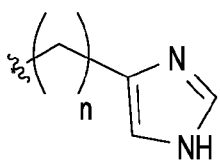
Figure 8D:
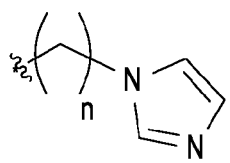
Figure 8E:
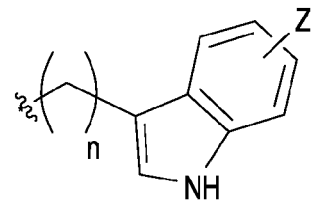
Figure 8F:
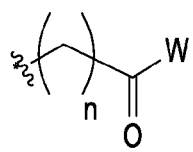
Figure 8G:
Figure 8H:
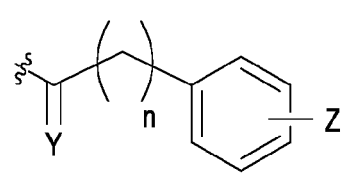
Figure 8I:
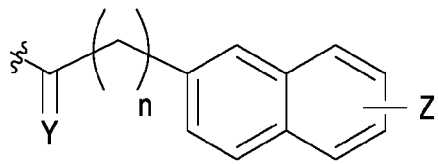
Figure 8J:
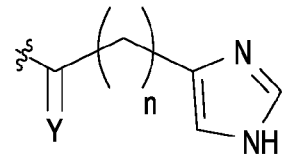
Figure 8K:
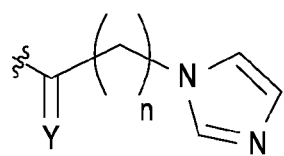
Figure 8L:
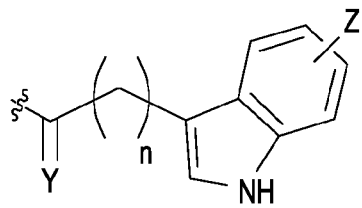
Figure 8M:
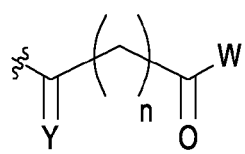
Figure 8N:
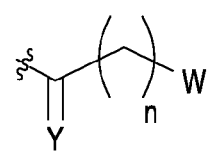

In FIG. 7, the synthesis of amphiphilic α-helix mimetics started with bromination of methyl 3-hydroxy-4-aminobenzoate compound 10 followed by displacement with an azide. An alkylation reaction using methyl N-Ac-4-amino-3-hydroxybenzoate compound 8 and a variety of alkyl halides and a base like NaH introduced a functional group corresponding to the i position of the α-helix. The methyl ester compound 16 was hydrolyzed by LiOH, and the methyl 3-azido-4-amino-5-hydroxybenzoate compound 17 was coupled with BOP. A second alkylation reaction added a functional group to the free 5-hydroxyl group corresponding to the i+3 (or i+4) position. A Staudinger coupling reaction using a suitable carboxylic acid and $PPh_3$ was used to place a functional group at the i+2 position. These steps were repeated to produce final amphiphilic α-helix mimetic compound 21. The incorporated hydrophilic functional groups not only results in a higher potency but also in a higher solubility in water. Corresponding compounds therefore require less organic solvent, which is an advantage for biological evaluation.

For example, the present invention includes an oligo-benzamide peptidomimetic compound having the following formula:

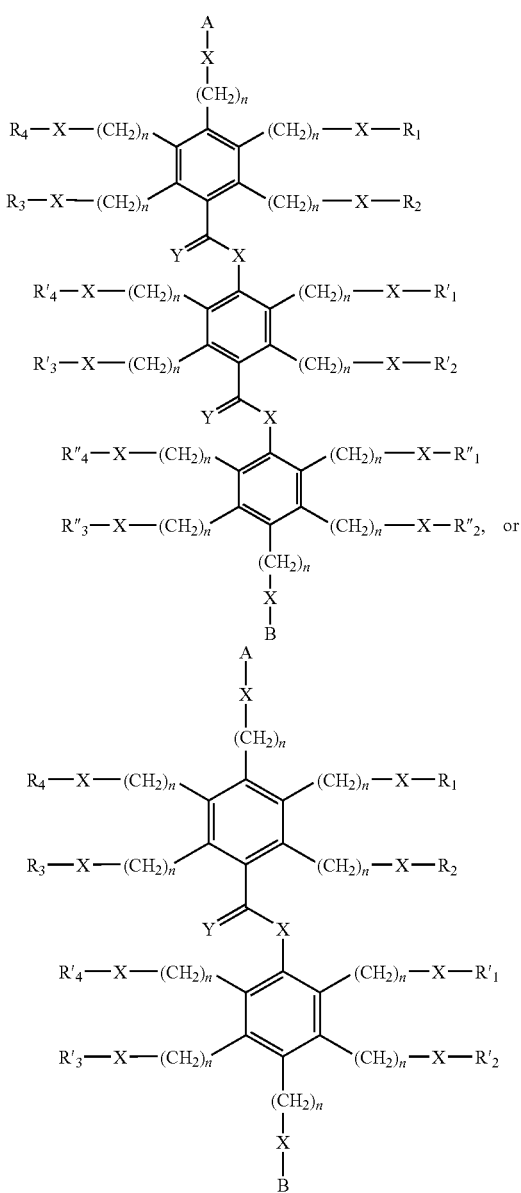

wherein X is independently a C, a N, a O, a S, a H, —$CH_2$—, —$CH_2CH_2$—, —CH═CH—, —C≡C—, —NH—, —NR—, —NH—NH—, —NH$(CH_2)_n$NH, —NR$(CH_2)_n$NR'— —NR—NR'—, —NH—O—, —NR—O—, —NH$(CH_2)_n$O—, —NR$(CH_2)_n$O—, —NH$(CH_2)_n$S—, —NR$(CH_2)_n$S—, —O$(CH_2)_n$O—, —O$(CH_2)_n$S—, —S (CH$_2$)$_n$S—, —CO—, —CO$_2$—, —COS—, —CONH—, —CONR—, —OC(O)NH—, —NHCONH—, —CONHCO—, —CO(CH$_2$)$_n$CO—, or combination thereof; wherein Y is independently a N, a O, a S or 2Hs; wherein R1, R2, R3, R4, R'1, R'2, R'3, R'4, R"1, R"2, R"3, and R"4, comprise independently a H, optionally substituted alkyl, lower alkyl, alkoxy, alkoxyalkyl, hydroxy, hydroxyalkyl, alkenyl, amino, imino, nitrate, alkylamino, dialkylamino, nitro, nitroso, aryl, biaryl, polycyclic aromatic, alkylaryl, arylalkyl, arylalkoxy, arylalkylamino, cycloalkyl, bridged cycloalkyl, cycloalkoxy, cycloalkyl-alkyl, arylthio, alkylthio, alkylsulfinyl, alkylsulfonyl, arylsulfonyl, arylsulfinyl, caboxamido, carbamoyl, carboxyl, carbonyl, alkoxycarbonyl, halogen, haloalkyl, haloalkoxy, heteroayl, heterocyclic ring, arylheterocyclic ring, heterocyclic compounds, amido, imido, guanidino, hydrazido, aminoxy, alkoxyamino, alkylamido, urea, carboxylic ester, thioethers, carboxylic acids, phosphoryl groups, polycyclic aromatic substituted with a OH, NH$_2$, SH, F, Cl, Br, I, NHR, NRR', CN$_3$H$_4$, a N, a O, a S, a H, or combination thereof. And, n is 0, 1, 2, 3, 4, 5, 6, 7 etc. For example R1, R2, R3, R4, R'1, R'2, R'3, R'4, R"1, R"2, R"3, and R"4, may include independently one or more of the structures listed in FIG. 8, where Z is a OH, NH$_2$, SH, F, Cl, Br or I; W is a OH, OR, NH$_2$, NHR, NRR' or CN$_3$H$_4$; n is 0, 1, 2, 3, 4, 5, 6, 7 etc.; and Y is a N, a O, a S or 2Hs.

"A" may be a substituent (R1, R2, R3, R4, R'1, R'2, R'3, R'4, R"1, R"2, R"3, or R"4), an acetyl, Boc (t-butoxycarbonyl), a Fmoc (9-fluorenylmethoxycarbonyl), a Cbz (benzyloxycarbonyl), an Aloc (allyloxycarbonyl), an amino acid, an amino acid analogue, an artificial amino acid, a dipeptide, a tripeptide, a tetrapeptide, or a pentapeptide. "A" may be a peptide sequence of between 2 and 30 amino acids that has greater than 50% homology to a portion of the BH3 sequence.

"B" may be a substituent (R1, R2, R3, R4, R'1, R'2, R'3, R'4, R"1, R"2, R"3, or R"4), an optionally substituted alkyl, lower alkyl, an optionally substituted C1-C7 alkyl, an amino acid, an amino acid analogue, an artificial amino acid, a dipeptide, a tripeptide, a tetrapeptide, or a pentapeptide; a peptide sequence of between 2 and 30 amino acids that has greater than 50% homology to a portion of the BH3 sequence; a linker of 1-20 amino acids, an optionally substituted C1-C7 alkyl or a linker as listed below:

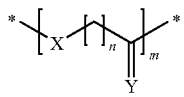

or a combination thereof, which may be optionally connected to one or more of the compounds or a combinations thereof.

One example of the chemical synthesis of the present invention is shown herein; however, the skilled artisan will be able to modify the synthetic scheme to create different functional groups and create the same product using different materials. $^1$H- and $^{13}$C-NMR spectra were recorded on a JEOL Model DELTA-270 (270 MHz) spectrometer. Tetramethylsilane (TMS) was used as the internal standard and the chemical shifts are listed in ppm. Data are expressed as follows: chemical shift (δ), multiplicity (s, singlet; d, doublet; dd, doublet of doublet; t, triplet; q, quartet; br s, broad singlet; m, multiplet), coupling constants (Hz). HRMS (FAB) were measured on JEOL HX-110 sector (EB). Silica gel used for column chromatography was Silica Gel Standard Grade (Sorbent Technologies, 230-400 mesh).

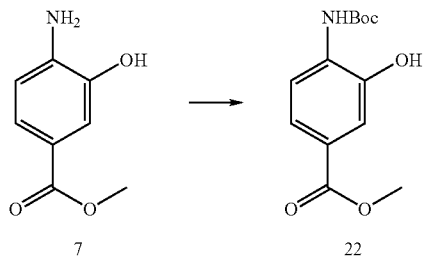

A solution of methyl 4-amino-3-hydroxy benzoate compound 7 (5 g, 30.0 mmol) and triethylamine (4.6 ml) in 100 ml CH$_2$Cl$_2$ was added drop-wise to a solution of di-tert-butyl dicarbonate (7.2 g, 32.9 mmol) in 20 ml CH$_2$Cl$_2$ at room temperature. After additional stirring for 12 hours at room temperature, the mixture was poured into water and extracted with CH$_2$Cl$_2$ (3×20 ml). The combined organic layers were washed with brine, dried over Na$_2$SO$_4$, filtered and concentrated under reduced pressure. The residue was purified by column chromatography (n-Hex/Ethyl Acetate (EA)=9/1 to n-Hex/EA=4/1) to give 7.2 g of compound 22 (90%).

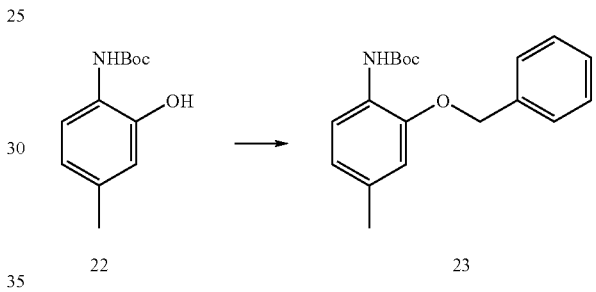

A solution of phenol compound 22 (0.20 g, 0.75 mmol) and NaH (33 mg in 60% oil, 0.82 mmol) in 10 ml dry DMF was stirred for 0.5 hours at room temperature and benzyl bromide (0.15 g, 0.82 mmol) was added slowly. The mixture was stirred for an additional hour and poured into water and extracted with ethyl acetate (3×20 ml). The combined organic layers were washed with brine, dried over Na$_2$SO$_4$, filtered, and concentrated under reduced pressure. The residue was purified by column chromatography (n-Hex/EA=9/1 to n-Hex/EA=4/1) to give 0.22 g of compound 23 (83%).

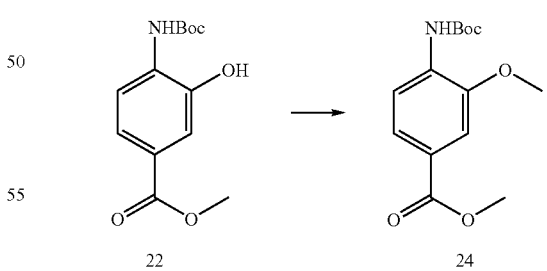

A solution of phenol compound 22 (0.2 g, 0.75 mmol) and NaH (33 mg in 60% oil, 0.82 mmol) in 10 ml dry DMF was stirred for 0.5 hour at room temperature and iodomethane (0.12 g, 0.82 mmol) was added slowly and the mixture was stirred for an additional hour. The mixture was diluted with water and extracted with ethyl acetate (3×20 ml). The combined organic layer was washed with brine, dried over Na$_2$SO$_4$, filtered, and concentrated under reduced pressure.

The residue was purified by column chromatography (n-Hex/EA=19/1) to give 0.18 g of compound 24 (86%).

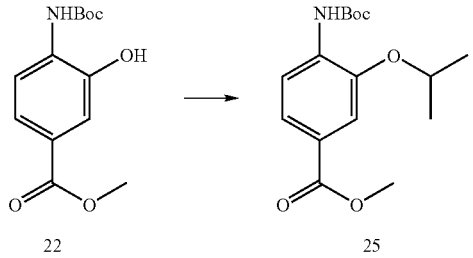

A solution of phenol compound 22 (0.2 g, 0.75 mmol) and NaH (33 mg in 60% oil, 0.82 mmol) were mixed in 10 ml dry DMF and stirred for 0.5 hours at room temperature. Then 2-bromopropane (0.22 g, 1.8 mmol) was added slowly and the mixture was stirred for an additional 24 hours, diluted with water and extracted with ethyl acetate (3×20 ml). The combined organic layer was washed with brine, dried over Na2SO4, filtered, and concentrated under reduced pressure. The residue was purified by column chromatography (n-Hex/EA=19/1) to give 0.18 g of compound 25 (78%).

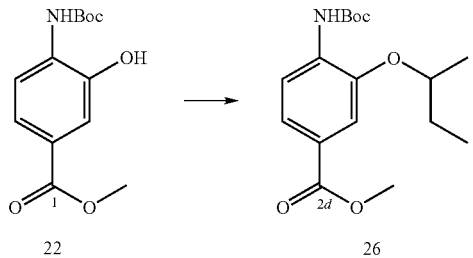

A solution of phenol compound 22 (0.2 g, 0.75 mmol) and NaH (33 mg in 60% oil, 0.82 mmol) was stirred in 10 ml dry DMF for 0.5 hour at room temperature and then 2-bromobutane (0.25 g, 1.8 mmol) was added slowly. The mixture was stirred for an additional 24 hours, diluted with water, extracted with ethyl acetate (3×20 ml), the combined organic layer was washed with brine, dried over $Na_2SO_4$, filtered, and concentrated under reduced pressure. The residue was purified by column chromatography (n-Hex/EA=19/1) to give 0.18 g of compound 26 (73%).

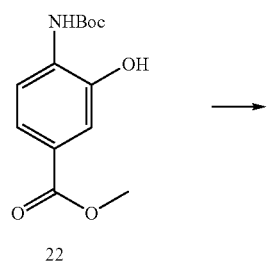

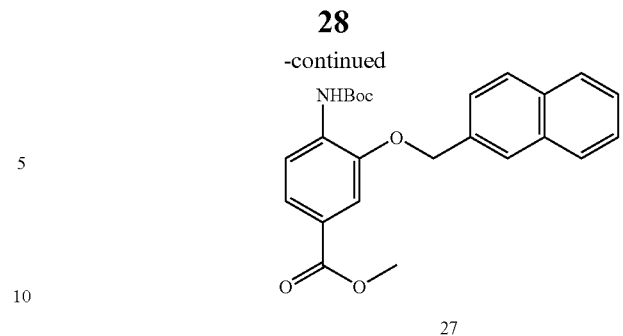

A solution of phenol compound 22 (0.2 g, 0.75 mmol) and NaH (33 mg in 60% oil, 0.82 mmol) was stirred in 10 ml dry DMF for 0.5 hours at room temperature and 2-bromomethylnaphtalene (0.18 g, 0.82 mmol) was added slowly. The mixture was stirred for an additional hour. The mixture was diluted with water, extracted with ethyl acetate (3×20 ml), and the combined organic layer was washed with brine, dried over $Na_2SO_4$, filtered and concentrated under reduced pressure. The residue was purified by column chromatography (n-Hex/EA=10/1 to n-Hex/EA=4/1) to give 0.25 g of compound 27 (82%).

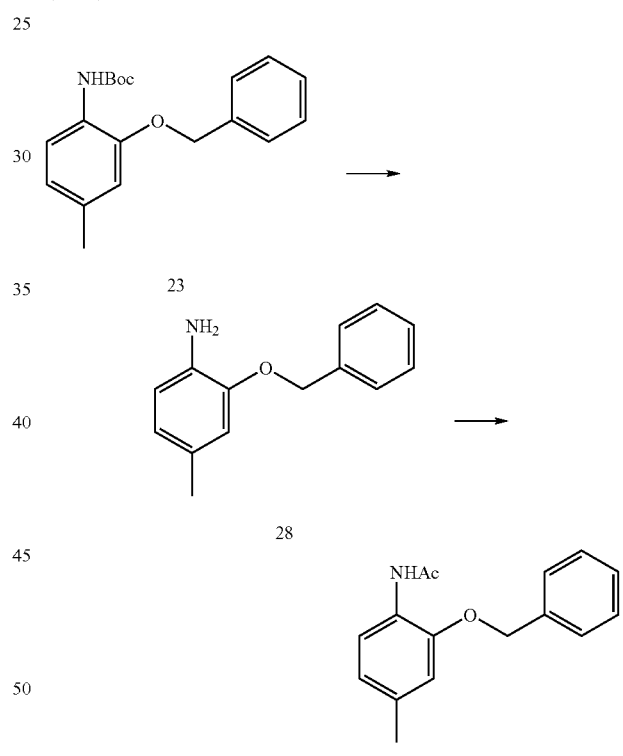

To a solution of compound 23 (2 g, 5.60 mmol) in 16 ml $CH_2Cl_2$, 4 ml trifluoroacetic acid was added in an ice-water bath. The reaction solution was stirred at room temperature for 2 hours and the excess trifluoroacetic acid and $CH_2Cl_2$ were removed under reduced pressure. The residue was dissolved in $CH_2Cl_2$, washed with saturated $NaHCO_3$ and brine and dried over $Na_2SO_4$. The organic layer was concentrated under reduced pressure to give the corresponding aniline, which was used in the next step without purification. A solution of aniline and DMAP (68 mg, 0.56 mmol) in acetic anhydride was stirred at room temperature for 12 hours. The reaction mixture was poured into water and extracted with $CH_2Cl_2$. The organic layer was washed with 1N HCl, water, and saturated $NaHCO_3$ solution, dried and concentrated to give compounds 28 and 29. The mixture was purified by column chromatography (n-Hex/EA=4/1 to n-Hex/EA=2/1) to give 1.62 g of compound 29 (97%).

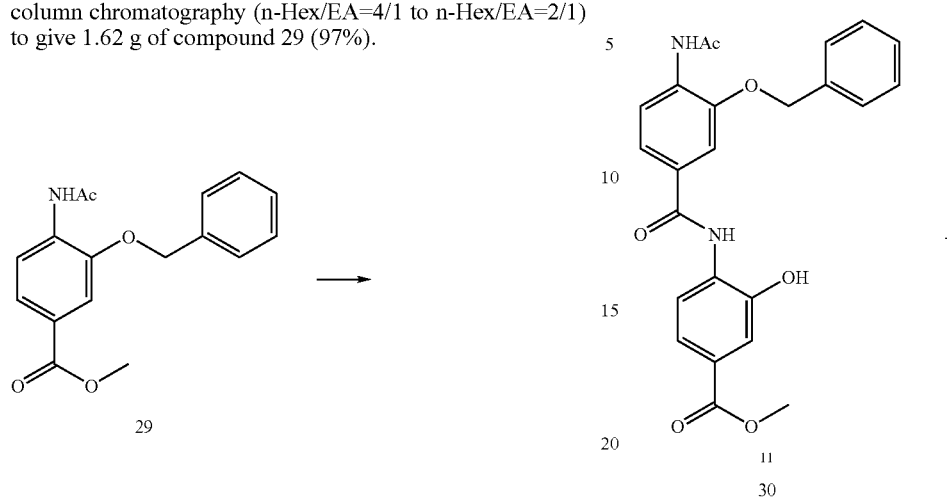

Compound 29 (1.62 g, 5.68 mmol) was dissolved in 1N NaOH (10 ml)/MeOH (20 ml)/THF (40 ml) and stirred at 60° C. for 2 hours. Methanol and THF were carefully concentrated and the mixture was acidified with 1N HCl, and the suspension was extracted with ethyl acetate, dried over $Na_2SO_4$ and evaporated under reduced pressure to give the corresponding acid, which was used in the next step without purification. The solution of acid, DMF (cat.) and $SOCl_2$ (2.7 g, 22.7 mmol) in 20 ml THF was heated at 60° C. for 2 hours. After the reaction mixture was cooled, the reaction mixture was concentrated under reduced pressure. The residue was dissolved in $CH_2Cl_2$ and cooled at 0° C. To this acid chloride DIPEA (5.14 g, 39.8 mmol) and methyl 4-amino-3-hydroxy-benzoate compound 7 (1.42 g, 8.51 mmol) were added and stirred at room temperature for 2 hours. The reaction mixture was concentrated under reduced pressure and the residue was purified by column chromatography (n-Hex/EA=2/1 to n-Hex/EA=1/1) to give 2.02 g of compound 30 (82% in three steps).

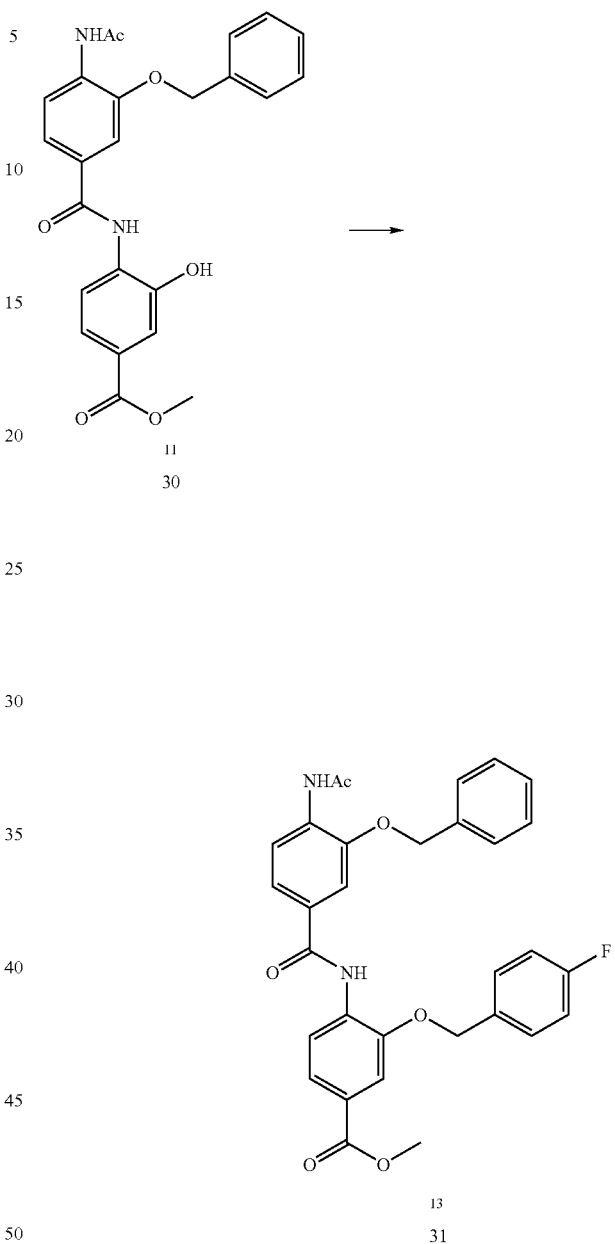

A solution of phenol compound 30 (1.93 g, 4.44 mmol) and NaH (0.20 g in 60% oil, 4.88 mmol) in 50 ml dry DMF was stirred for 0.5 hour at room temperature and then 4-fluorobenzyl bromide (1.01 g, 5.33 mmol) was added slowly. The mixture was stirred for an additional 2 hours, diluted with water, and extracted with ethyl acetate (3×40 ml). The combined organic layer was washed with brine, dried ($Na_2SO_4$) and concentrated under reduced pressure. The residue was purified by column chromatography (n-Hex/EA=4/1 to n-Hex/EA=2/1) to give 1.86 g of compound 31 (77%).

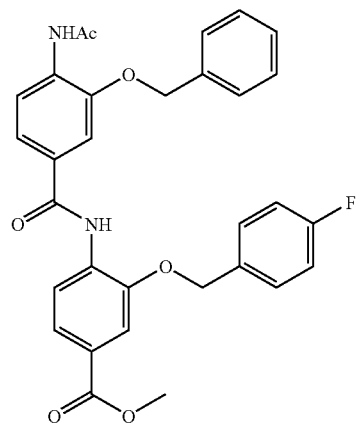

31

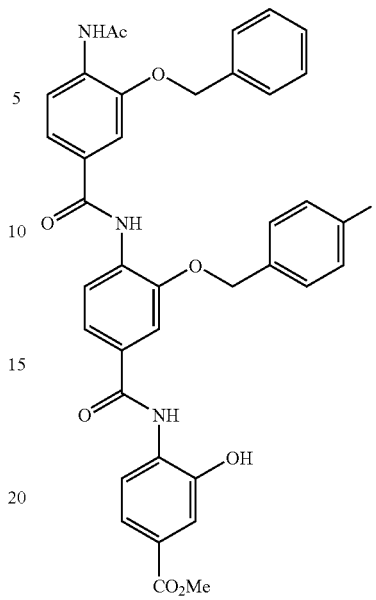

32

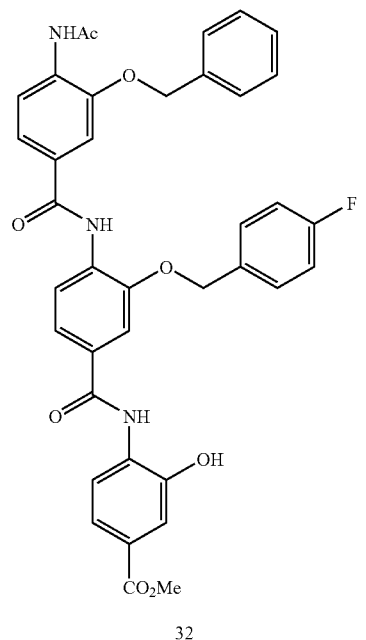

32

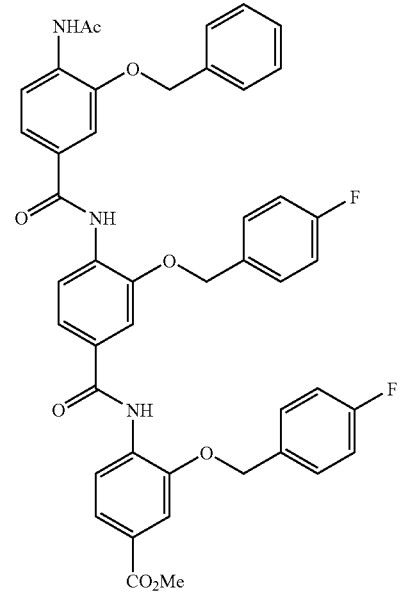

33

Dimer compound 31 (1.86 g, 3.43 mmol) was dissolved in 1N NaOH (10 ml)/MeOH (20 ml)/THF (40 ml) and heated at 60° C. for 2 hours. Methanol and THF were carefully concentrated and the mixture was acidified with 1N HCl, and the suspension was extracted with ethyl acetate, dried over $Na_2SO_4$ and evaporated under reduced pressure to give the corresponding acid, which was used in the next step without purification. The solution of acid, BOP (1.92 g, 4.11 mmol) and DIPEA (1.11 g, 8.57 mmol) in $CH_2Cl_2$ was stirred at 0° C. for 0.5 hour. Methyl 4-amino-3-hydroxybenzoate compound 7 (0.57 g, 2.86 mmol) was added and stirred at room temperature for 2 hours. The mixture was poured into water and extracted with $CH_2Cl_2$ (3×40 ml), and the combined organic layer was washed with brine, dried over $Na_2SO_4$, filtered, and concentrated under reduced pressure. The residue was purified by column chromatography (dichloromethane/ethyl ether=19/1) to give 1.72 g of compound 32 (74% in two steps).

A solution of phenol compound 32 (1.72 g, 2.54 mmol) and NaH (0.11 g in 60% oil, 2.79 mol) in 50 ml dry DMF was stirred for 0.5 hours at room temperature and then 4-fluorobenzyl bromide (3.05 mmol) was added slowly. The mixture was stirred for an additional 2 hours. The mixture was diluted with water and extracted into ethyl acetate (3×40 ml). The combined organic layer was washed with brine, dried (Na2SO4) and concentrated under reduced pressure. The residue was purified by column chromatography (dichloromethane/ethyl ether=19/1) to give 1.20 g of compound 33 (61%).

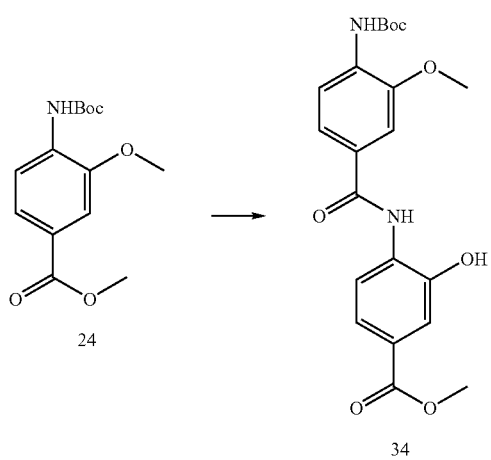

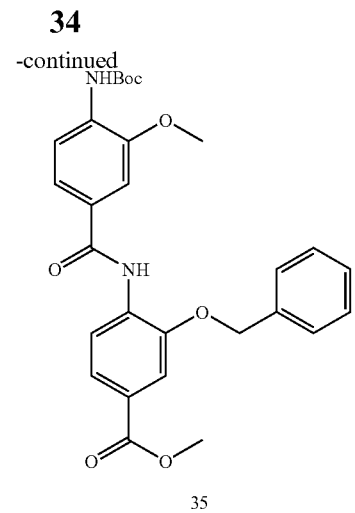

Compound 24 (2 g, 7.11 mmol) was dissolved in 1N NaOH (10 ml)/MeOH (20 ml)/THF (40 ml) and heated at 60° C. for 2 hours. Methanol and THF were carefully concentrated and the mixture was acidified with 1N HCl. The suspension was extracted with ethyl acetate, dried over Na2SO4 and evaporated under reduced pressure to give the corresponding acid, which was used in the next step without purification. The solution of acid, DMF (cat.) and SOCl2 (3.38 g, 28.4 mmol) in 20 ml THF was heated at 60° C. for 2 hours. The reaction mixture was cooled and concentrated under reduced pressure. The residue was dissolved in CH2Cl2 and cooled at 0° C. To this acid chloride DIPEA (9.19 g, 71.1 mmol) and methyl 4-amino-3-hydroxybenzoate compound 7 (1.42 g, 8.53 mmol) were added and stirred at room temperature for 2 hours. The reaction mixture was concentrated under reduced pressure and purified by column chromatography (n-Hex/EA=4/1 to n-Hex/EA=2/1) to give 2.28 g of compound 34 (77% in three steps).

A solution of compound 34 (2.28 g, 5.48 mmol) and NaH (0.24 g in 60% oil, 6.02 mol) in 50 ml dry DMF was stirred for 0.5 hour at room temperature and benzyl bromide (1.13 g, 6.57 mmol) was added slowly. The mixture was stirred for an additional 2 hours, diluted with water and extracted with ethyl acetate (3×40 ml). The combined organic layer was washed with brine, dried (Na2SO4) and concentrated under reduced pressure. The residue was purified by column chromatography (n-Hex/EA=4/1 to n-Hex/EA=2/1) to give 2.21 g of compound 35 (80%).

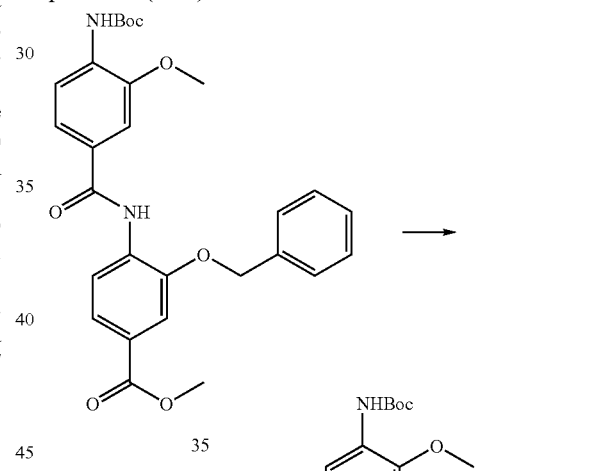

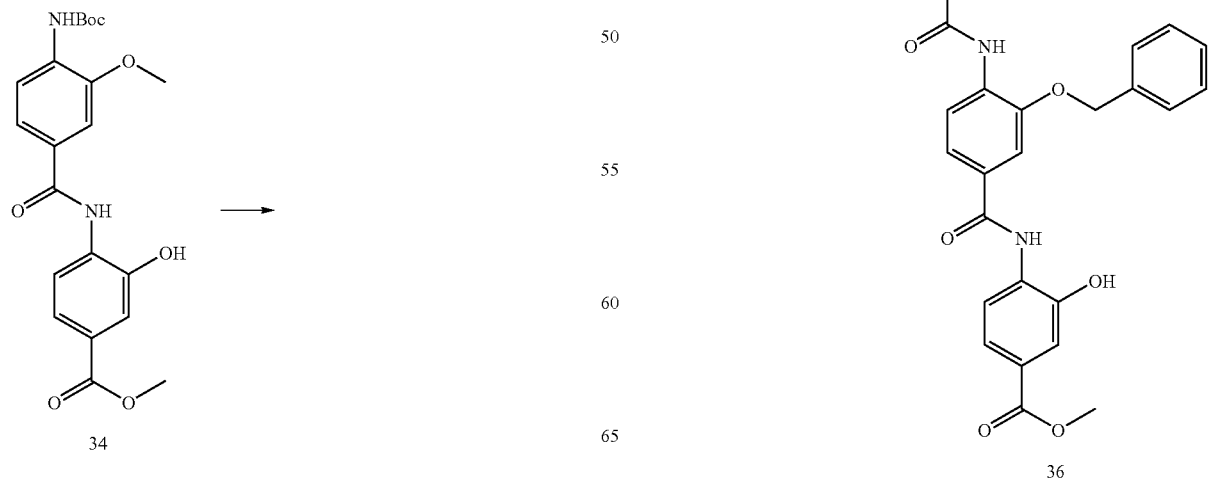

Compound 35 (2.21 g, 4.49 mmol) was dissolved in 1N NaOH (10 ml)/MeOH (20 ml)/THF (40 ml) and heated at 60° C. for 2 hours. Methanol and THF were carefully concentrated and the mixture was acidified with 1N HCl. The suspension was extracted with ethyl acetate, dried over Na2SO4 and evaporated under reduced pressure to give the corresponding acid, which was used in the next step without purification. The solution of acid, DMF (cat.) and SOCl2 (2.14 g, 17.9 mmol) in 20 ml THF was refluxed for 2 hours. The reaction mixture was cooled and concentrated under reduced pressure. The residue was dissolved in CH2Cl2 and cooled at 0° C. To this acid chloride, DIPEA (5.80 g, 44.9 mmol) and methyl 4-amino-3-hydroxybenzoate 5 (0.90 g, 5.38 mmol) were added and stirred at room temperature for 2 hours. The reaction mixture was concentrated under reduced pressure and purified by column chromatography (n-Hex/EA=9/1 to n-Hex/EA=2/1) to give 2.19 g of compound 36 (76% in three steps).

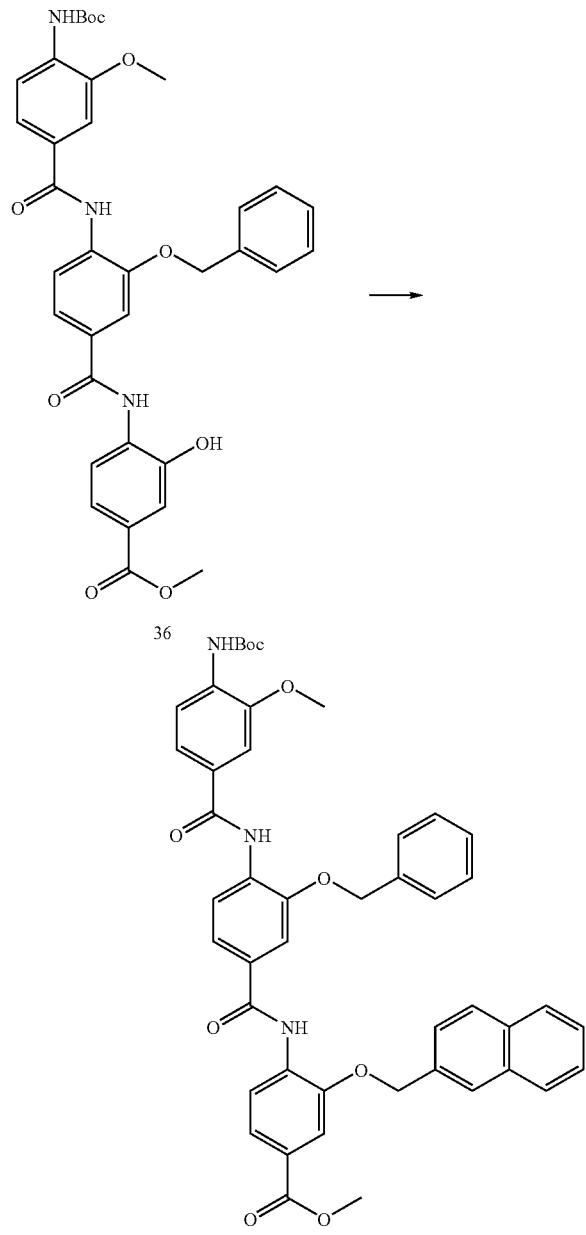

A solution of trimer compound 36 (2.19 g, 3.41 mmol) and NaH (0.15 g in 60% oil, 3.75 mmol) in 50 ml dry DMF was stirred for 0.5 hour at room temperature. 2-bromomethyl naphthalene (0.91 g, 4.10 mmol) was added slowly to the solution. The solution was stirred for an additional 2 hours, diluted with water and extracted with ethyl acetate (3×40 ml). The combined organic layer was washed with brine, dried (Na2SO4) and concentrated under reduced pressure. The residue was purified by column chromatography (n-Hex/EA=4/1 to n-Hex/EA=1/1) to give 2.29 g of compound 37 (86%).

The synthesis of benzamides includes an alkylation reaction to place a functional group corresponding to an amino acid in a helix. The reaction is given below:

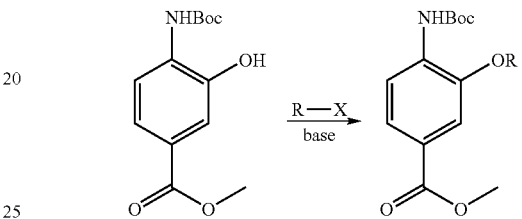

Figure 9A:
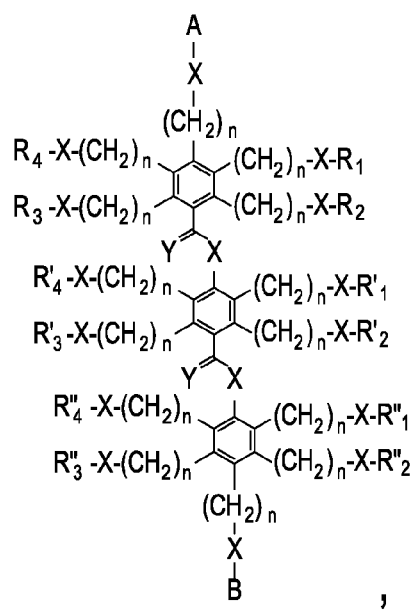
FIGS. 9A-9AD are illustrations of some embodiments of the present invention.
Figure 9B:
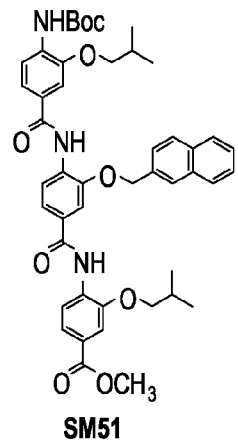
Figure 9C:
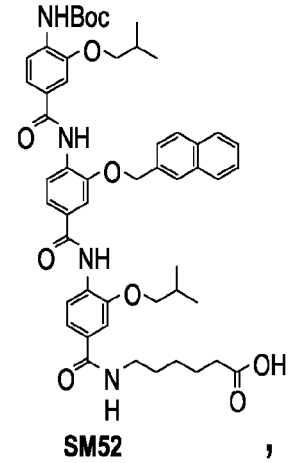
Figure 9D:
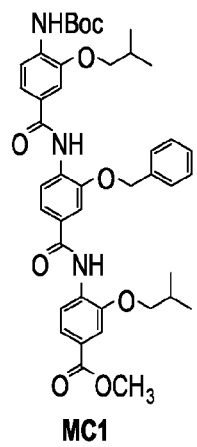
Figure 9E:
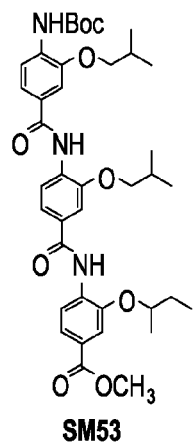
Figure 9F:
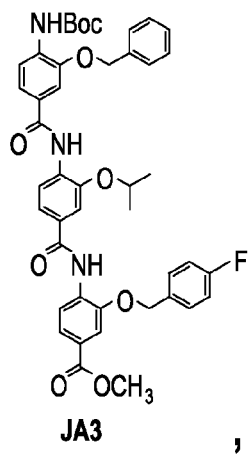
Figure 9G:
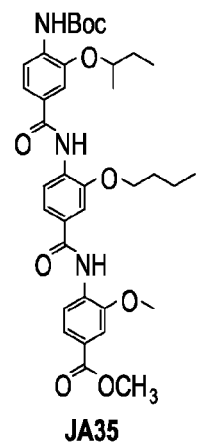
Figure 9H:
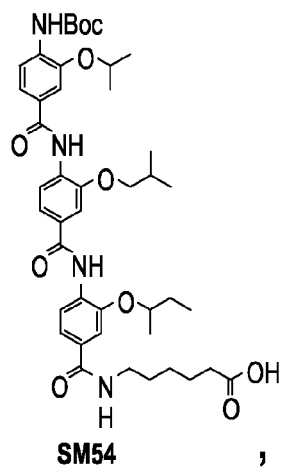
Figure 9I:
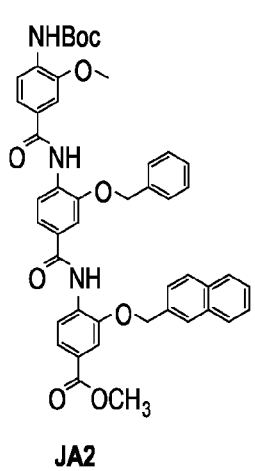
Figure 9J:
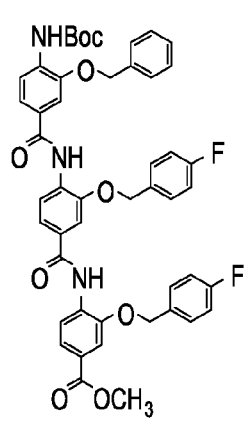
Figure 9K:
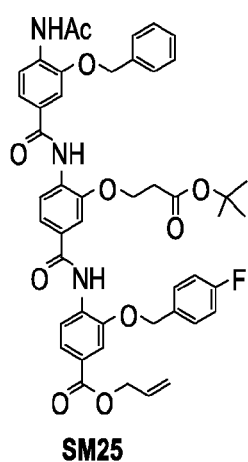
Figure 9L:
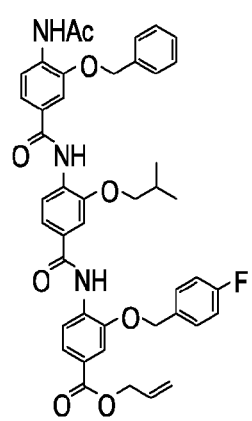
Figure 9M:
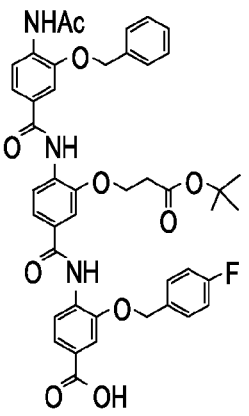
Figure 9N:
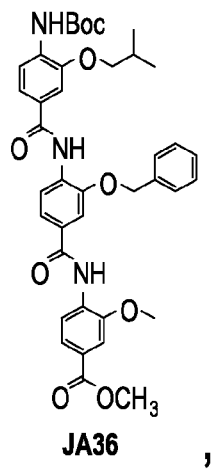
Figure 9O:
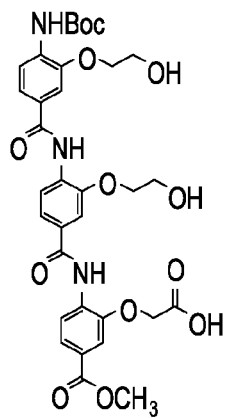
Figure 9P:
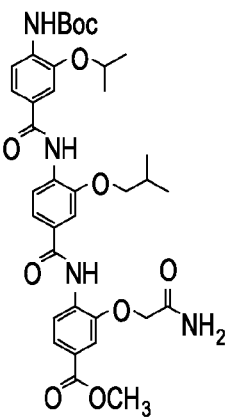
Figure 9Q:
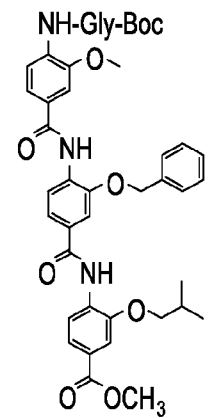
Figure 9R:
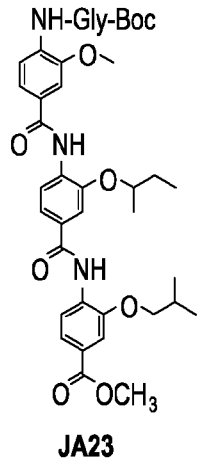
Figure 9S:
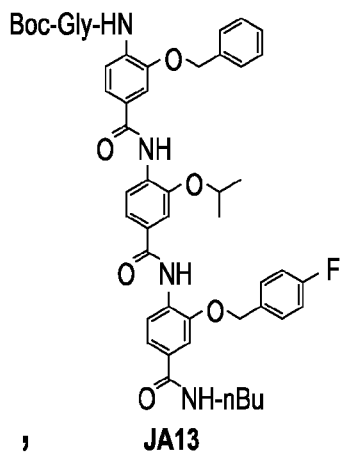
Figure 9T:
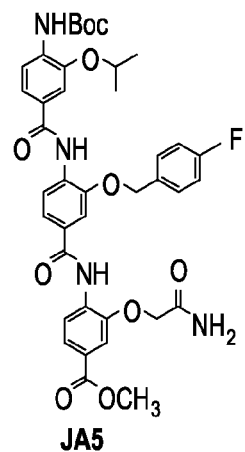
Figure 9U:
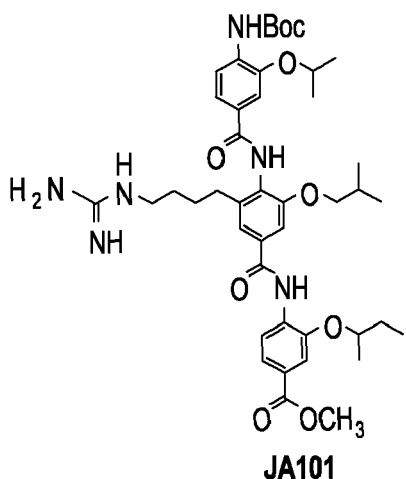
Figure 9V:
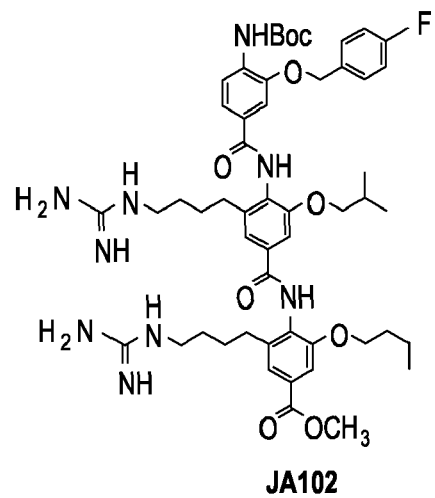
Figure 9W:
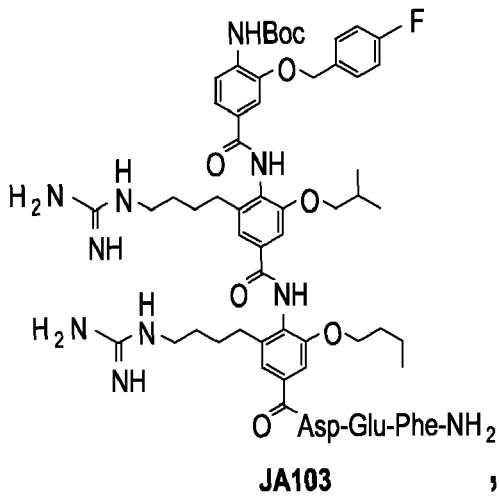
Figure 9X:
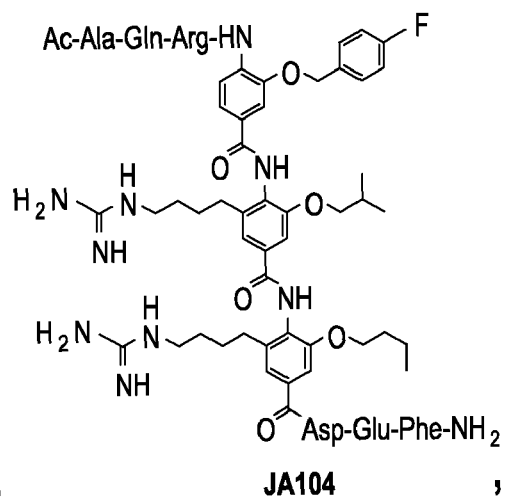
Figure 9Y:
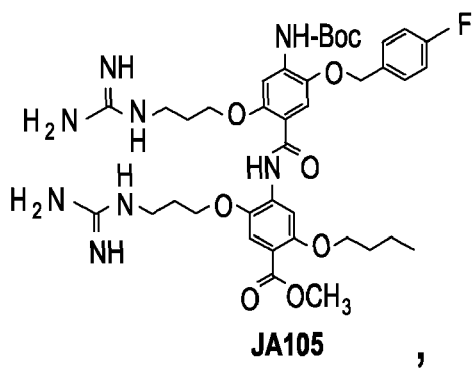
Figure 9Z:
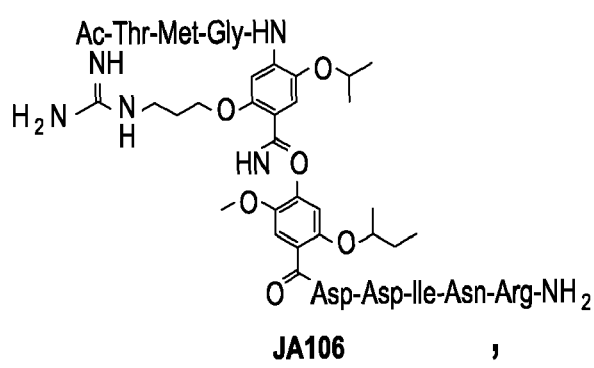
Figure 9A:
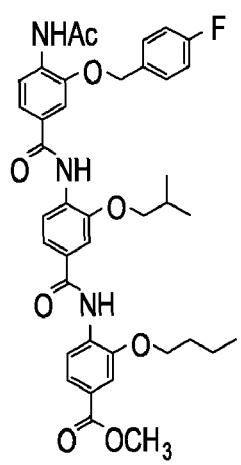
Figure 9A:
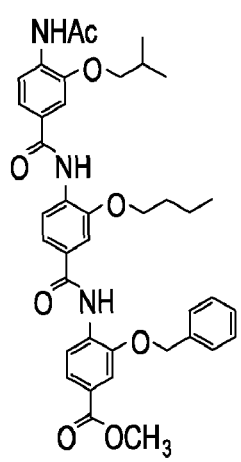
Figure 9A:
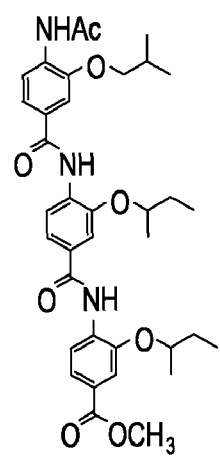
Figure 9A:
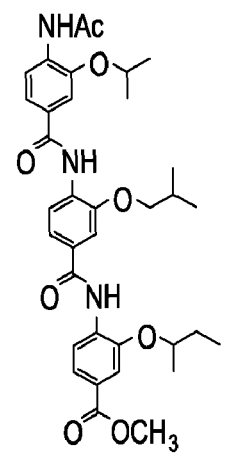
Figure 10:
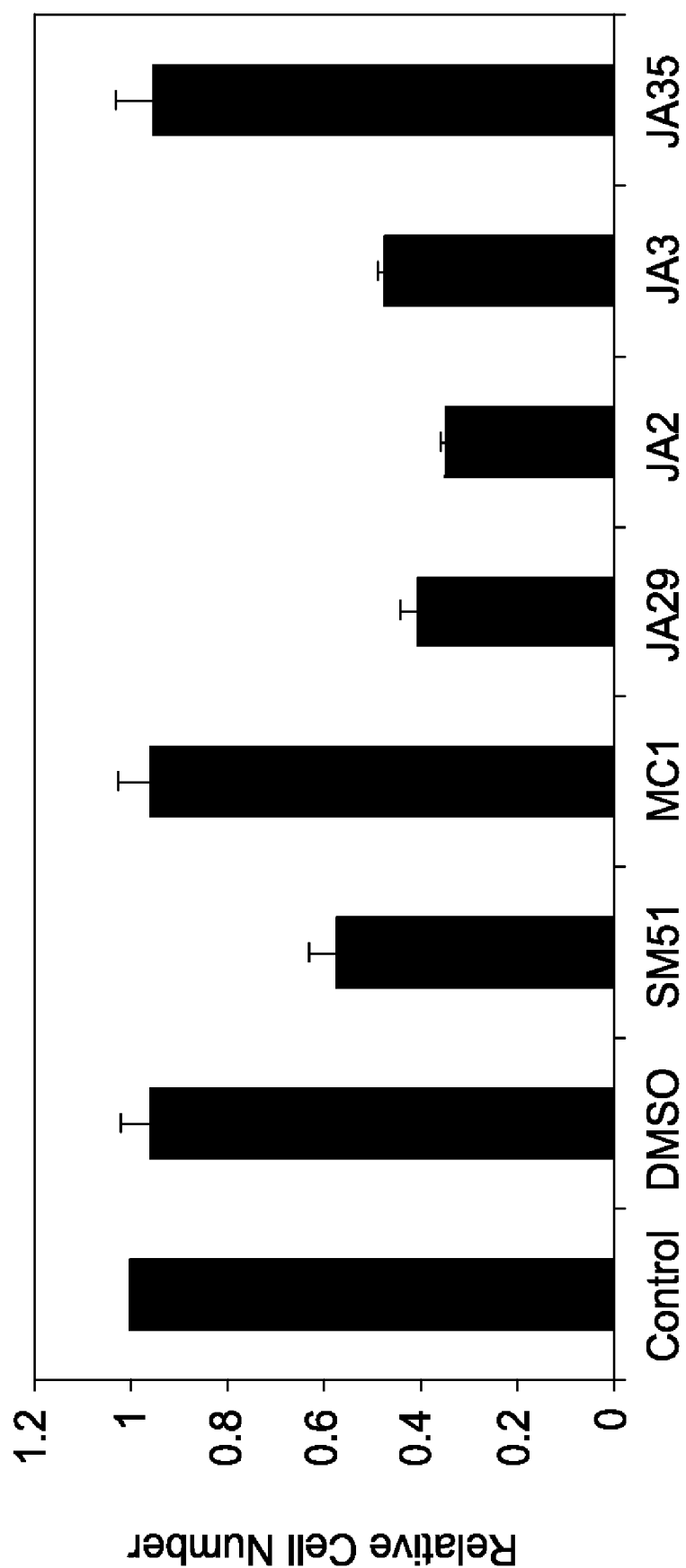
FIG. 10 is a graph of the functional screening of oligo-benzamide α-helix mimetics on prostate cancer cells.
Figure 11A:
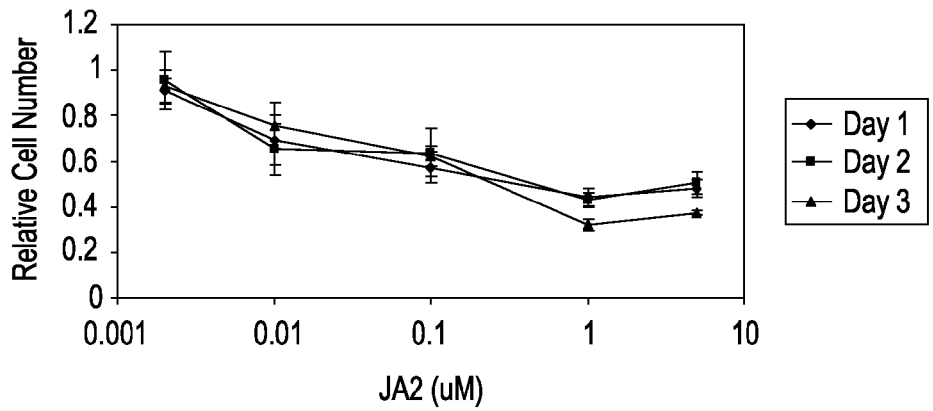
FIGS. 11A-11G are graphs of the functional screening of oligo-benzamide α-helix mimetics on prostate cancer cells in dose-dependent manner.
Figure 11B:
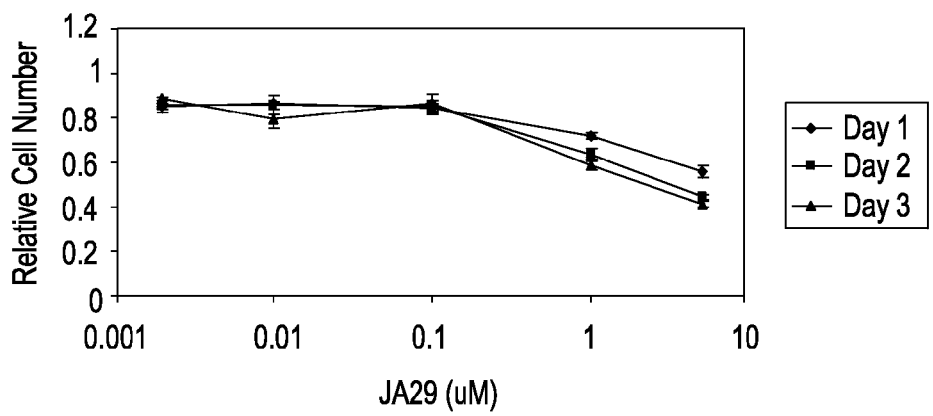
Figure 11C:
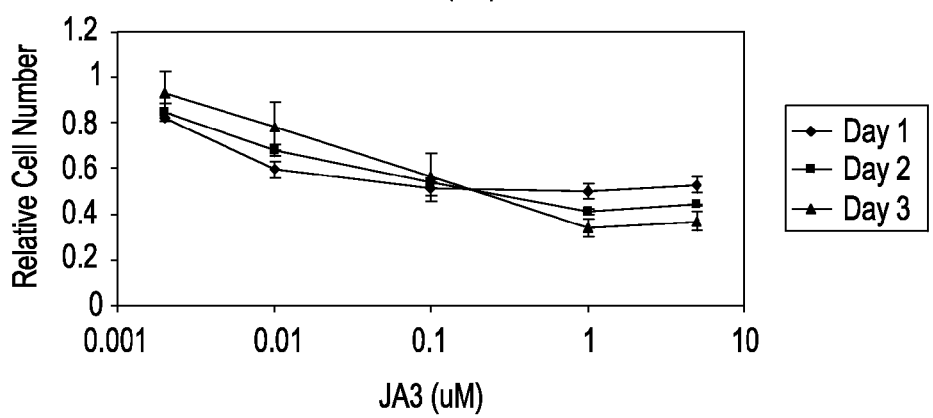
Figure 11D:
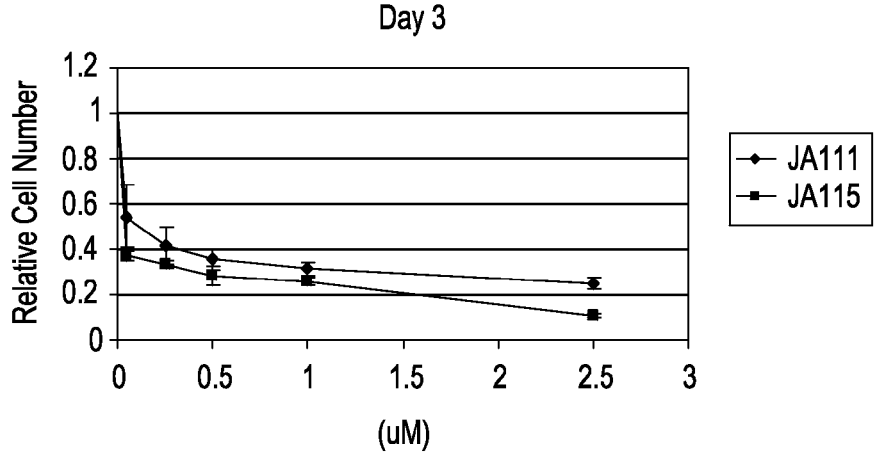
Figure 11E:
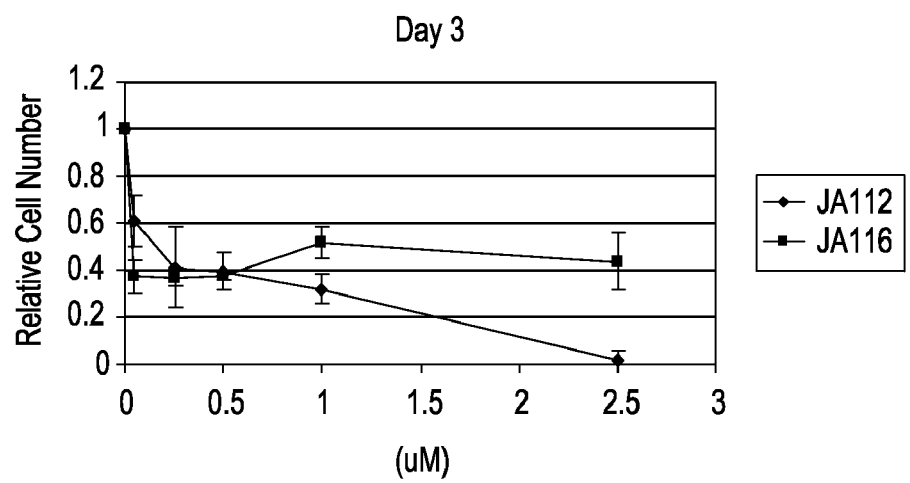
Figure 11F:
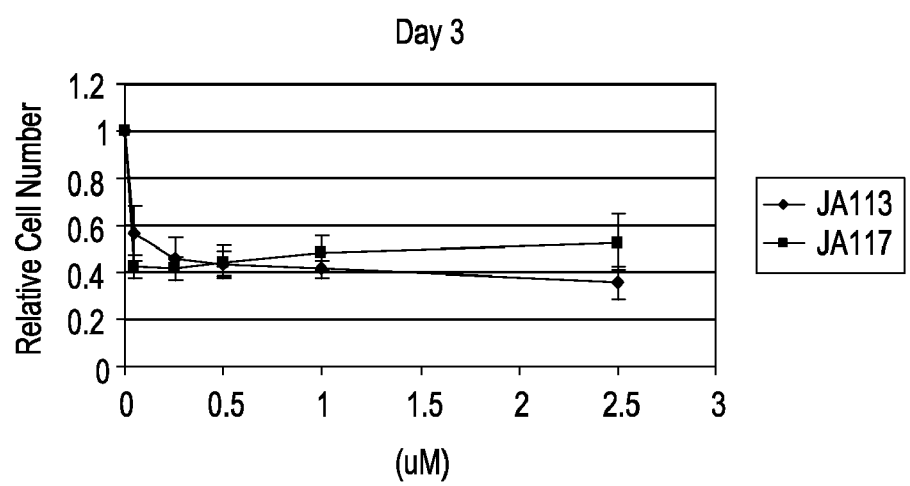
Figure 11G:
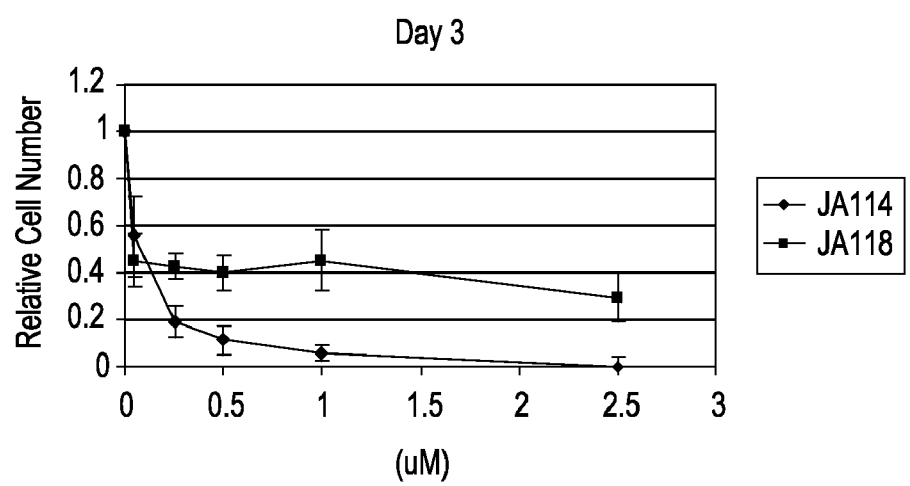

FIGS. 9A-9AD are illustrations of some embodiments of the instant invention. To explore the therapeutic potential, the α-helix peptidomimetic compounds of various BH3 domains were tested for their effect on various tumor cells including prostate cancer cells. The MTT assay was setup in a high throughput mode by using the epMotion automated pipetting and the SpectraMax M5 microplate reader, which is ready for robot plate feeder. Using MTT assay, the effects of the compounds were first screened on cancer cells including prostate cancer cells (PC3) at concentration of 2 nM-25 μM. Among many compounds screened, a typical result was illustrated in FIG. 10. As shown in FIG. 10, significant suppressions on PC3 cells were found for compound SM51, JA29, JA2 and JA3. These compounds consistently produced higher inhibitory effects on PC3 cells and were further analyzed for their dose responds with MTT assay. As shown in FIG. 11, several compounds suppressed PC3 cells in a dose-dependent manner, as determined during three-day treatment. The $IC_{50}$ was found at about 100 nM (for JA2 and JA3), 2 μM (for JA29), 40 nM (for JA112), 50 nM (for JA114) and 30 nM (for JA115).

FIG. 10 is a graph of the functional screening of the α-helix peptidomimetics on cancer cells. Prostate cancer cells (PC3) were plated in 96-well plate by epMotion automated pipetting 5070 (Eppendorf) and cultured overnight. 5 μM of each compound was added to the culture of PC3 cells in 96 well-plate. The cell number was determined by MTT assay after 24 hours treatment of the compound. The MTT reading was carried out by using SpectraMax M5 microplate reader (Molecular Devices).

FIGS. 11A-11G are graphs of the functional screening of α-helix peptidomimetics on cancer cells in dose-dependent manner. Compound JA2, JA29, JA3, JA111, JA112, JA113, JA114, JA115, JA116, JA117, and JA118 suppress prostate cancer cells (PC3) in dose-dependent manner. The compounds were added to the PC3 cells at the indicated concentration. MTT assay was carried out after treatment of 24, 48 and 72 hours. The relative cell number was determined by comparing to untreated control.

These results indicate that cancer cells including the prostate cancer cells are sensitive towards the designed α-helix peptidomimetic compounds based on the α-helical BH3 domains, suggesting a potential therapeutic application of the designed α-helix peptidomimetics for a treatment of cancers including prostate cancer.

To mimic α-helices in the BH3 domain, we have already developed a scaffold, oligo-benzamides. Substitution on the rigid oligo-benzamides allowed us to develop one-sided α-helix peptidomimetics presenting amino acids found at the i, i+3 or i+4, and i+7 positions, and amphiphilic α-helix peptidomimetics presenting the i, i+2, i+3 or i+4, i+5, and i+7 positions.

To explore the therapeutic potential, the α-helix peptidomimetic compounds of various BH3 domains were tested for their effect on various tumor cells including prostate cancer cells. The MTT assay was setup in a high throughput mode by using the epMotion automated pipetting and the SpectraMax M5 microplate reader, which is ready for robot plate feeder. Using MTT assay, the effects of the compounds were first screened on cancer cells including prostate cancer cells at concentration of 2 nM-25 μM. These BH3 peptidomimetics showed high cytotoxicity and several compounds showed $IC_{50}$=30–100 nM.

These results indicate that cancer cells including the prostate cancer cells are sensitive towards the designed α-helix peptidomimetic compounds based on the α-helical BH3 domains, suggesting a potential therapeutic application of the designed α-helix peptidomimetics for a treatment of cancers including prostate cancer.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A compound of the formula:

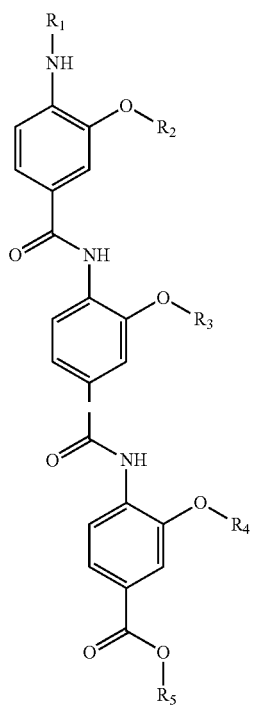

wherein $R_1$ is H, Boc, Boc-Gly, a substituted or unsubstituted lower alkylcarbonyl group, or a substituted or unsubstituted arylalkyl group, $R_2$ is H, a substituted or unsubstituted lower alkyl group, a substituted or unsubstituted benzyl group, or a substituted or unsubstituted arylalkyl group, $R_3$ is a H, a substituted or unsubstituted lower alkyl group, a substituted or unsubstituted benzyl group, or a substituted or unsubstituted arylalkyl group, $R_4$ is a H, a substituted or unsubstituted alkyl group, a substituted or unsubstituted benzyl group, or a substituted or unsubstituted arylalkyl group, and $R_5$ is a H, a substituted or unsubstituted alkyl group, a substituted or unsubstituted benzyl group, a substituted or unsubstituted arylalkyl group, or $CH_2CH\!=\!CH_2$.

2. The compound of claim 1, formulated with one or more of diluents excipients, active agents, lubricants, preservatives, stabilizers, wetting agents, emulsifiers, salts for influencing osmotic pressure, buffers, colorings, flavorings, aromatic substances, penetration enhancers, surfactants, fatty acids, bile salts, chelating agents, colloids and combinations thereof.

3. The compound of claim 1, formulated as a solution, an emulsion, a liposome-containing formulation, a tablet, a capsule, a gel capsule, a liquid syrup, a soft gel, a suppository, an enema, a patch, an ointment, a lotion, a cream, a gel, a drop, a spray, a liquid or a powder.

4. An oligo-benzamide compound selected from:

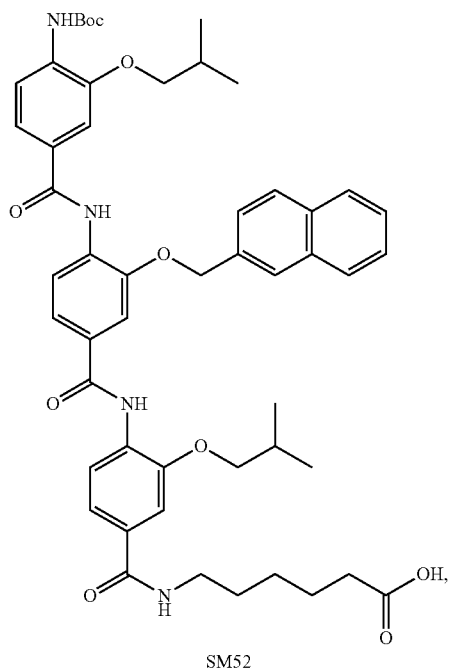
SM52

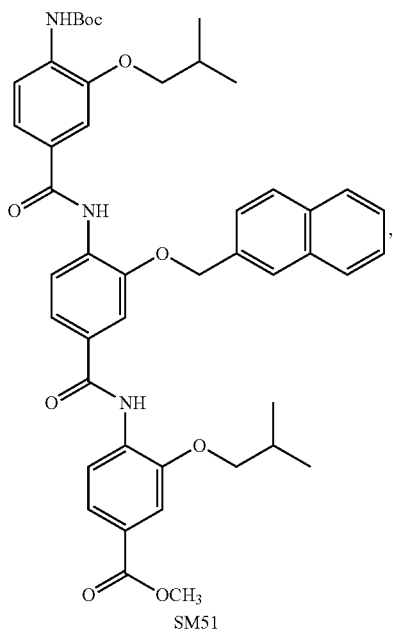
SM51

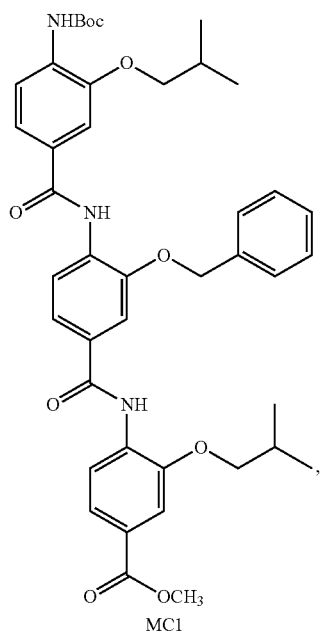
MC1

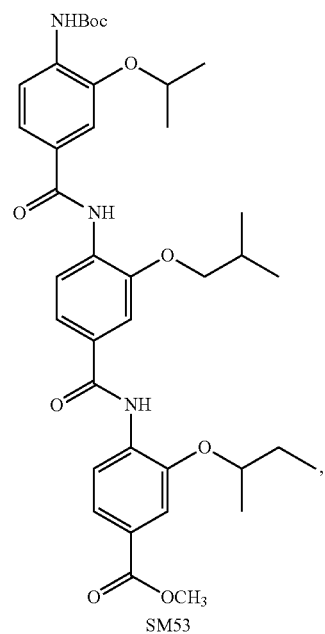
SM53
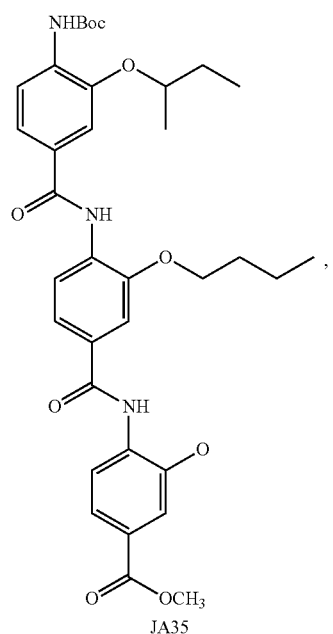
JA35
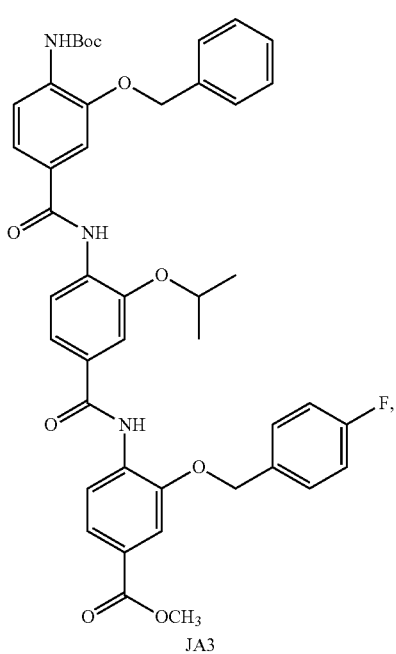
JA3
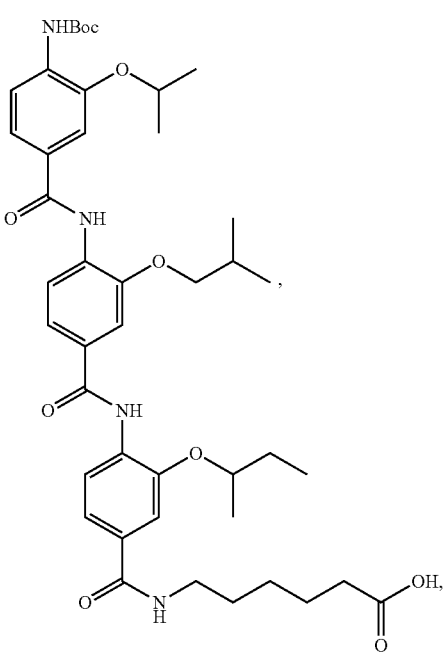
SM54

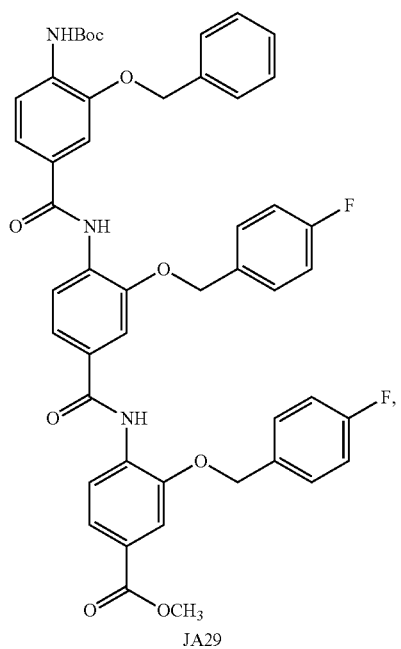
JA29
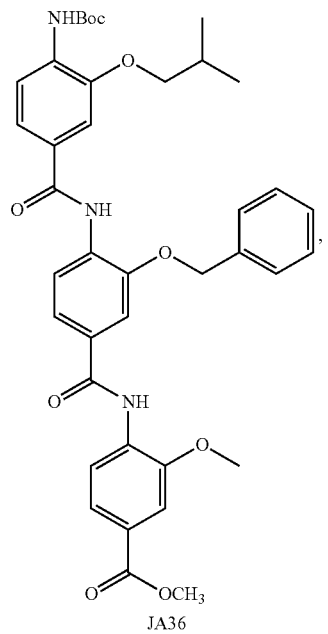
JA36
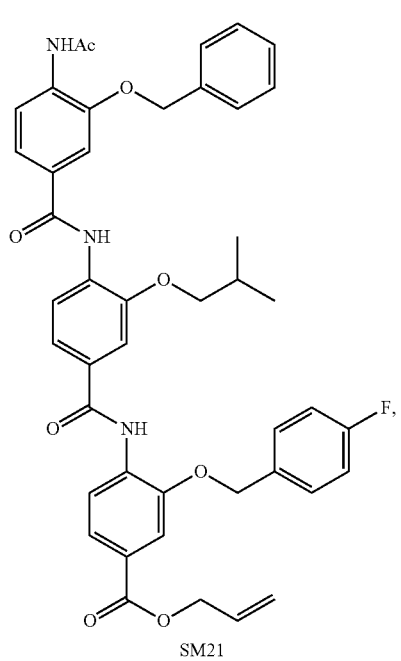
SM21
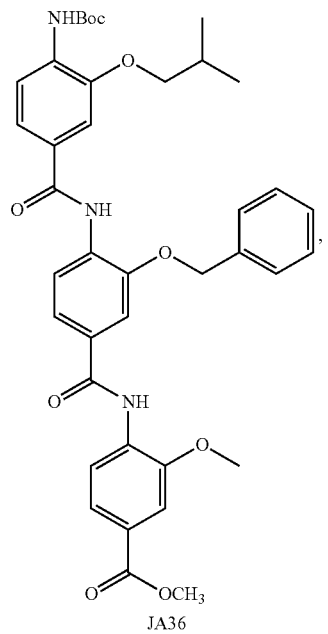
JA20

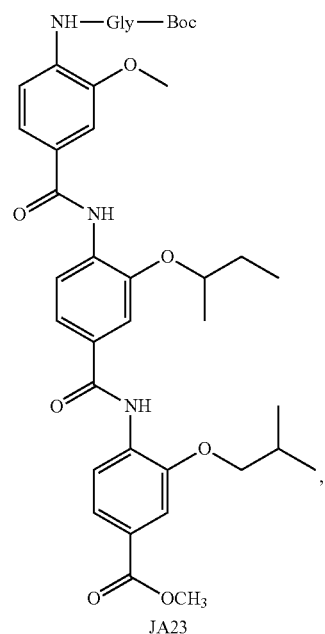
JA23
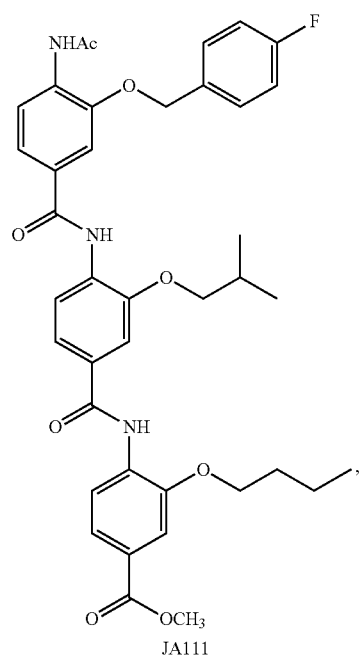
JA111
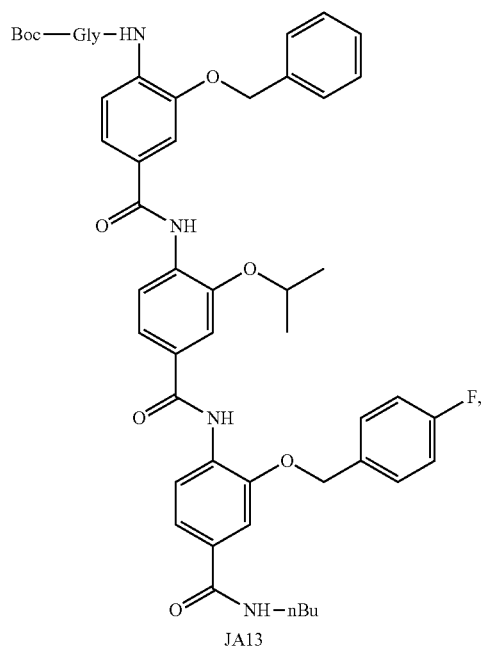
JA13
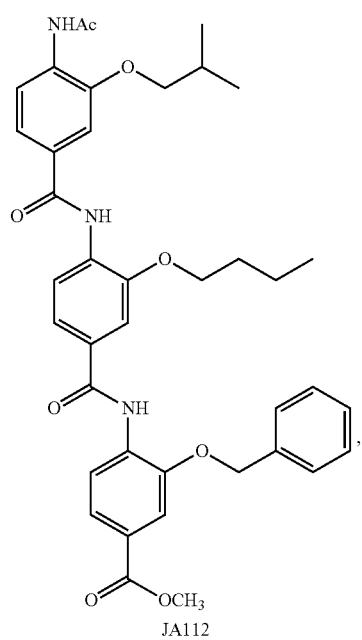
JA112

-continued

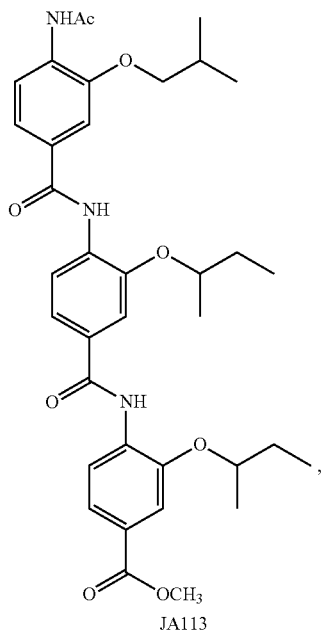
JA113 and

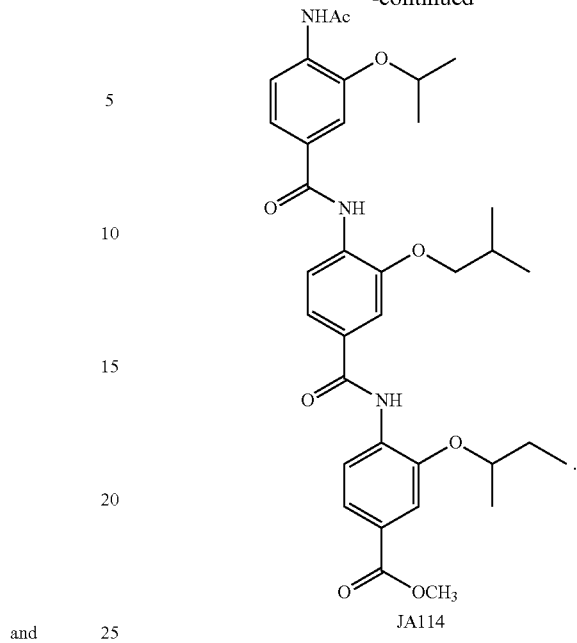
JA114

5. The compound of claim 4, formulated with one or more of diluents excipients, active agents, lubricants, preservatives, stabilizers, wetting agents, emulsifiers, salts for influencing osmotic pressure, buffers, colorings, flavorings, aromatic substances, penetration enhancers, surfactants, fatty acids, bile salts, chelating agents, colloids and combinations thereof.

6. The compound of claim 4, wherein the compound is formulated as a solution, an emulsion, a liposome-containing formulation, a tablet, a capsule, a gel capsule, a liquid syrup, a soft gel, a suppository, an enema, a patch, an ointment, a lotion, a cream, a gel, a drop, a spray, a liquid or a powder.

* * * * *

UNITED STATES PATENT AND TRADEMARK OFFICE
CERTIFICATE OF CORRECTION

PATENT NO. : 8,236,983 B2
APPLICATION NO. : 12/353173
DATED : August 7, 2012
INVENTOR(S) : Jung-Mo Ahn It is certified that error appears in the above-identified patent and that said Letters Patent is hereby corrected as shown below:

In claim 1, column 38, lines 39-66, delete chemical drawing and insert

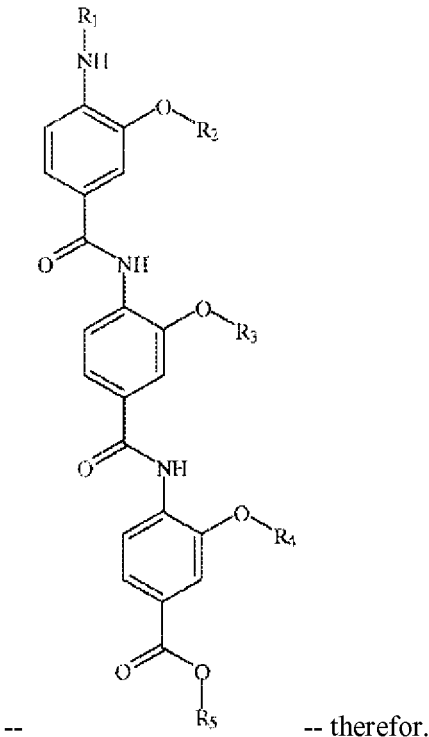

-- therefor.

Signed and Sealed this
Thirteenth Day of November, 2012

David J. Kappos
*Director of the United States Patent and Trademark Office*

CERTIFICATE OF CORRECTION (continued)
U.S. Pat. No. 8,236,983 B2

In claim 4, column 42, lines 4-29, delete chemical drawing and insert

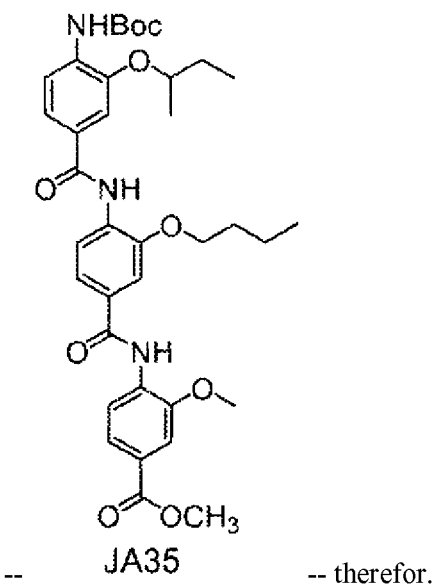

-- therefor.